US012016688B2

(12) United States Patent
Weinberger

(10) Patent No.: US 12,016,688 B2
(45) Date of Patent: Jun. 25, 2024

(54) IN VIVO RADICAL DOSIMETRY AND IN VIVO HYDROXYL RADICAL PROTEIN FOOT-PRINTING

(71) Applicant: GenNext Technologies, Inc., Half Moon Bay, CA (US)

(72) Inventor: Scot Randy Weinberger, Montara, CA (US)

(73) Assignee: GENNEXT TECHNOLOGIES, INC., Half Moon Bay, CA (US)

( * ) Notice: Subject to any disclaimer, the term of this patent is extended or adjusted under 35 U.S.C. 154(b) by 429 days.

(21) Appl. No.: 17/411,855

(22) Filed: Aug. 25, 2021

(65) Prior Publication Data

US 2021/0378558 A1 Dec. 9, 2021

Related U.S. Application Data

(63) Continuation-in-part of application No. 17/168,472, filed on Feb. 5, 2021, which is a continuation-in-part
(Continued)

(51) Int. Cl.
*A61B 5/145* (2006.01)
*A61B 5/1455* (2006.01)
(Continued)

(52) U.S. Cl.
CPC ........ *A61B 5/1455* (2013.01); *A61B 5/14546* (2013.01); *G01N 21/631* (2013.01);
(Continued)

(58) Field of Classification Search
CPC .............. A61B 5/14546; A61B 5/1455; A61B 2562/0233; G01N 21/53; G01N 21/631; G01N 21/645; G01N 33/6803
See application file for complete search history.

(56) References Cited

U.S. PATENT DOCUMENTS 2,987,456 A 6/1961 Lauer
3,354,315 A 11/1967 Preston et al.
(Continued)

FOREIGN PATENT DOCUMENTS

EP 0347039 A3 12/1989
GB 2358244 A 7/2001
(Continued)

OTHER PUBLICATIONS

Zhang, H., et al., Fast photochemical oxidation of proteins for comparing structures of protein-ligand complexes: the calmodulin-peptide model system. Anal Chem, 2011. 83(1): p. 311-8.
(Continued)

*Primary Examiner* — Mark R Gaworecki
(74) *Attorney, Agent, or Firm* — Rimon Law, P.C.

(57) ABSTRACT

Systems and methods of in vivo hydroxyl radical protein foot-printing are presented. These teachings may be used to, for example, study three-dimensional protein structure or bio-kinetics. Radical Dosimetry including an optional intrinsic standard is used on isolated intact cells. Real-time feedback based on an internal standard provides comparability between different experiments and in vivo analysis results in data that is representative of actual biological conditions.

30 Claims, 7 Drawing Sheets

Related U.S. Application Data of application No. PCT/US2020/012430, filed on Jan. 6, 2020, and a continuation-in-part of application No. PCT/US2019/057059, filed on Oct. 18, 2019, which is a continuation-in-part of application No. 16/316,006, filed on Jan. 7, 2019, now Pat. No. 10,816,468, said application No. PCT/US2020/012430 is a continuation-in-part of application No. 16/316,006, filed as application No. PCT/US2018/034682 on May 25, 2018, now Pat. No. 10,816,468.

(60) Provisional application No. 63/128,439, filed on Dec. 21, 2020, provisional application No. 62/788,219, filed on Jan. 4, 2019, provisional application No. 62/747,247, filed on Oct. 18, 2018, provisional application No. 62/511,571, filed on May 26, 2017.

(51) Int. Cl.
   G01N 21/63   (2006.01)
   G01N 33/68   (2006.01)
   G01N 21/53      (2006.01)
   G01N 21/64      (2006.01)

(52) U.S. Cl.
   CPC .. G01N 33/6803 (2013.01); *A61B 2562/0233* (2013.01); *G01N 21/53* (2013.01); *G01N 21/645* (2013.01)

(56) References Cited

U.S. PATENT DOCUMENTS

| | | | |
|---|---|---|---|
| 4,000,973 | A | 1/1977 | Petersen |
| 5,021,646 | A | 6/1991 | Weinberger et al. |
| 5,037,100 | A | 8/1991 | Hlousek |
| 5,037,523 | A | 8/1991 | Weinberger et al. |
| 5,443,791 | A | 8/1995 | Cathcart et al. |
| 5,602,446 | A | 2/1997 | Kolber et al. |
| 5,807,750 | A | 9/1998 | Baum et al. |
| 5,936,728 | A | 8/1999 | Bouzid |
| 6,254,689 | B1 | 7/2001 | Meder |
| 6,741,347 | B1 | 5/2004 | Scaiano et al. |
| 7,812,311 | B2 | 10/2010 | DeCamp et al. |
| 7,817,270 | B2 | 10/2010 | Gusev |
| 8,446,587 | B2 | 5/2013 | Gusev |
| 9,279,814 | B2 | 3/2016 | Brenowitz et al. |
| 10,851,335 | B2 | 12/2020 | Jones et al. |
| 2002/0033369 | A1 | 3/2002 | Bender |
| 2003/0036206 | A1 | 2/2003 | Chien et al. |
| 2003/0074062 | A1 | 3/2003 | Monzyk |
| 2004/0241872 | A1 | 12/2004 | Wegrzyn et al. |
| 2005/0218082 | A1 | 10/2005 | Williamson et al. |
| 2005/0266065 | A1 | 12/2005 | Perrier et al. |
| 2006/0257877 | A1 | 11/2006 | Anderle |
| 2007/0152154 | A1 | 7/2007 | DeCamp et al. |
| 2008/0165363 | A1 | 7/2008 | Gusev |
| 2009/0074611 | A1 | 3/2009 | Monzyk et al. |
| 2010/0081159 | A1 | 4/2010 | Ledebeva et al. |
| 2010/0137163 | A1 | 6/2010 | Link et al. |
| 2013/0119277 | A1 | 5/2013 | Atzler et al. |
| 2014/0030751 | A1* | 1/2014 | Sharp .................. G01N 33/6848 435/23 |
| 2018/0079998 | A1 | 3/2018 | Jones et al. |

FOREIGN PATENT DOCUMENTS

| | | |
|---|---|---|
| JP | 2009192259 A | 8/2009 |
| WO | 2016/130553 A1 | 8/2016 |
| WO | 2016/164244 A1 | 10/2016 |
| WO | 2018/218163 A1 | 11/2018 |
| WO | 2020/142785 A1 | 7/2020 |
| WO | 2020/146425 A1 | 7/2020 |

OTHER PUBLICATIONS

Johnson, D.T., L.H. Di Stefano, and L.M. Jones, Fast photochemical oxidation of proteins(FPOP): A powerful mass spectrometry based structural proteomics tool. J Biol Chem, 2019.

Espino, J.A. and L.M. Jones, Illuminating Biological Interactions with in Vivo Protein Footprinting. Anal Chem, 2019. 91(10): p. 6577-6584.

Chea E.E. and L.M. Jones, Modifications generated by fast photochemical oxidation of proteins reflect the native conformations of proteins. Protein Sci, 2018. 27(6): p. 1047-1056.

Chea, E.E. and L.M. Jones, Analyzing the structure of macromolecules in their native cellular environment using hydroxyl radical footprinting. Analyst, 2018. 143(4): p. 798-807.

Aprahamian, M.L., et al., Rosetta Protein Structure Prediction from Hydroxyl Radical Protein Footprinting Mass Spectrometry Data. Anal Chem, 2018. 90(12): p. 7721-7729.

Rinas, A., et al., Development of a Microflow System for In-Cell Footprinting Coupled with Mass Spectrometry. Anal Chem, 2016. 88(20): p. 10052-10058.

Rinas, A., J.A. Espino, and L.M. Jones, An efficient quantitation strategy for hydroxyl radical-mediated protein footprinting using Proteome Discoverer. Anal Bioanal Chem, 2016. 408(11): p. 3021-31.

Rinas, A. and L.M. Jones, Fast photochemical oxidation of proteins coupled to multidimensional protein identification technology (MudPIT): expanding footprinting strategies to complex systems. J Am Soc Mass Spectrom, 2015. 26(4): p. 540-6.

Espino, J.A., V.S. Mali, and L.M. Jones, In Cell Footprinting Coupled with Mass Spectrometry for the Structural Analysis of Proteins in Live Cells. Anal Chem, 2015. 87(15): p. 7971-7978.

Jones, L.M., et al., Fast photochemical oxidation of proteins for epitope mapping. Anal Chem, 2011. 83(20): p. 7657-61.

Poor, T.A., et al., Probing the paramyxovirus fusion (F) protein-refolding event from pre- to postfusion by oxidative footprinting. Proc Natl Acad Sci U S A, 2014. 111(25): p. E2596-605.

Jones, L.M., et al., Complementary MS methods assist conformational characterization of antibodies with altered S-S bonding networks. J Am Soc Mass Spectrom, 2013. 24(6): p. 835-45.

Cong, M. et al., Research on A Novel R-0 Wafer Handling Robot, Aug. 2007, 2007 IEEE International Conference on Automation and Logistics, pp. 597-602 (Year: 2007).

Sharp, et al. Real Time Normalization of Fast Photochemical Oxidation of Proteins Experiments by Inline Adenine Radical Dosimetry, Analytical Chemistry, vol. 90, pp. 12625-12630, Oct. 5, 2018.

Roush, et al., Intrinsic Buffer Hydroxyl Radical Dosimetry Using Tris(Hydroxymethyl)Aminomethane, bioRxiv, pp. 1-6, Oct. 19, 2019.

PCT/US2019/057059, International Search Report and Written Opinion, mailed Dec. 31, 2019.

PCT/US2020/012430, International Search Report and Written Opinion, mailed Mar. 12, 2020.

EP 18805903.4, Extended European Search Report, mailed Jan. 29, 2021.

EP 18805903.4, Response to Extended European Search Report, mailed Jan. 29, 2021, filed Jun. 9, 2021.

EP 18805903.4, First Examination Report, mailed Oct. 21, 2021.

EP 18805903.4, Response to First Examination Report, mailed Oct. 21, 2021, filed Jan. 26, 2022.

EP 23172498.0, Extended European Search Report, mailed Jul. 3, 2023.

EP 18805903.4, Response to Extended European Search Report, mailed Jan. 29, 2021, filed Sep. 25, 2023.

EP 20735970.4, Extended European Search Report, mailed Sep. 9, 2022.

EP 20735970.4, Response to Extended European Search Report, dated Sep. 9, 2022, mailed Mar. 27, 2023.

JP2021-539578, Office Action, mailed Oct. 31, 2023 plus translation.

PCT/US2021/060394, International Search Report and Written Opinion, mailed Mar. 24, 2022.

(56) References Cited

OTHER PUBLICATIONS

Xu et al., "Hydroxyl radical-mediated modification of proteins as probes for structural proteomics", Chemical Reviews, 2007, vol. 107, No. 8, pp. 3514-3543.

Takamoto et al., "Radiolytic protein footprinting with mass spectrometry to probe the structure of macromolecular complexes", Annu. Rev. Biophys. Biomol Struct. 2006, 35:251-76.

Niu et al., "Dosimetry determines the inital OH radical concentration in fast photochemical oxidation of proteins (FPOP)", J. Am. Soc. Mass Spectrom. (2015) 26:843-846.

U.S. Appl. No. 13/951,708, Final Rejection dated Feb. 10, 2015.

Gau et al., "Fast photochemical oxidation of protein footprints faster than protein unfolding", Anal. Chem. 2009, 81, 6563-6571.

U.S. Appl. No. 11/970,676, Non-final Office Action dated Apr. 1, 2009.

Hambly et al. Laser flash photolysis of hydrogen peroxide to oxidize protein solvent-accessible residues on the microsecond timescale:, J Am Soc Mass Spectrom 2005, 16, 2057-2063.

Scaiano, Dr. J.C., "Laser Flash Photolysis: From Lindqvist to Luzchem", technical report No. 001, Luzchem Research, Inc., Ottawa, Canada, Aug. 2003.

Vahidi,et al., "Probing the time scale of FPOP (fast photochemical oxidation of proteins): radical reactions extend over tens of milliseconds", J. Am. Soc. Mass Spectrom. (2016) 27:1156-1164.

Li, et al., "High Structural Resolution Hydroxyl Radical Protein Footprinting Reveals an Extended Robo1-Heparin Binding Interface" JBC Papers in Press. Published on Mar. 9, 2015 as Manuscript M115.648410.

Wang, et al. "Oligomeric Structure of the Chemokine CCL5/RANTES from NMR, MS, and SAXS Data", Structure 19, 1138-1148, Aug. 10, 2011.

Li, et al., "Structural analysis of the glycosylated intact HIV-1 gp120-b12 antibody complex using hydroxyl radical protein footprinting", Biochemistry 2017, 56, 957-970.

Watson, et al., "Conformational analysis of therapeutic proteins by hydroxyl radical protein footprinting", the AAPS Journal, vol. 14, No. 2, Jun. 2012.

Xie, et al., "Hydroxyl radical dosimetry for high flux hydroxyl radical protein footprinting applications using a simple optical detection method", Anal. Chem. 2015, 87, 10719-10723.

Sharp, et al., "Analysis of protein solvent accessible surfaces by photochemical oxidation and mass spectrometry", Anal. Chem. 2004 76, 672-683.

Huang, et al., "An approach for separation and complete structural sequencing of Heparin/Heparin sulfate-like Oligosaccharides", 2013 Anal. Chem. 85 5787-5795.

Li, et al. "Improved identification and relative quantification of sites of peptide and protein oxidation for hydroxyl radical footprinting", 2013 J. Am Soc. Mass Spectrom.24 1767-1776.

Wang, et al., "Chemokine oligomerization in cell signaling and migration", Prog. Mol. Bioil. Transf. Sci. 117: 531-578, 2013.

Saladino, et al., "Aliphatic Peptidyl Hydroperoides as a source of secondary oxidation in hydroxyl radical protein footprinting", 2009 J. Am Soc. Mass Spectrom.20 1123-1126.

Watson, et al., Pulsed electron beam water radiolysis for submicrosecond hydroxyl radical protein footprinting:, 2009 Anal. Chem. 81, 2496-2505.

Bern, et al., "Conversion of methionine into homocysteic acid in heavily oxidized proteomics samples", Rapid. Commun. Mass Spectrom, 2010, 24, 768-772.

Charvatova, et al., "Quantifying protein interface footprinting by hydroxyl radical oxidation and molecular dynamics simulation: application to galectin-1", J. Am. Soc. Mass Spectrom, 2008, 19: 1692-1705.

Smedley, et al., "Probing the pH-dependent prepore to pore transition of bacillus anthracis protective antigen with differential oxidative protein footprinting", Biochemistry 2008, 47, 10694-10704.

U.S. Appl. No. 13/951,708, SB08 Form Filed Oct. 21, 2014.

JP2021-539578, Argument and Amendment filed in response to Office Action, mailed Oct. 31, 2023, filed Mar. 12, 2024, plus translation.

* cited by examiner

IN VIVO RADICAL DOSIMETRY AND IN VIVO HYDROXYL RADICAL PROTEIN FOOT-PRINTING

CROSS REFERENCE TO RELATED APPLICATIONS

This application is a Continuation-in-Part of U.S. Non-Provisional application Ser. No. 17/168,472 filed on Feb. 5, 2021 which is a Continuation-in-Part of PCT/US2020/012430 filed on Jan. 6, 2020 which is a Continuation-in-Part of U.S. Non-Provisional application Ser. No. 16/316,006 filed on Jan. 7, 2019, now U.S. Pat. No. 10,816,468 issued on Oct. 27, 2020 and also claims benefit and priority to U.S. Provisional Application No. 62/788,219 filed on Jan. 4, 2019; U.S. application Ser. No. 17/168,472 is also a Continuation-in-Part of PCT/US2019/057059 filed on Oct. 18, 2019 and also claims benefit and priority to U.S. Provisional Application No. 63/128,439 filed Dec. 21, 2020; PCT/US2019/057059 is also a Continuation-in-Part of U.S. application Ser. No. 16/316,006 and also claims benefit and priority to U.S. Provisional Application No. 62/788,219 and further claims benefit and priority to U.S. Provisional Application No. 62/747,247 filed on Oct. 18, 2018; U.S. application Ser. No. 16/316,006 is a 371 entry of PCT/US2018/034682 filed on May 25, 2018 which claims benefit and priority to U.S. Provisional Application No. 62/511,571 filed May 26, 2017. All of the foregoing disclosures are hereby incorporated herein by reference.

STATEMENT REGARDING FEDERALLY SPONSORED RESEARCH AND DEVELOPMENT

The invention described in this patent application was made with support from the U.S. government through National Institute of General Medical Sciences grant awards R43 GM 137728-01 and R44 GM 137728-02. As such, the U.S. government has certain rights to the invention.

BACKGROUND

Field of the Invention

The present invention relates to a device and methodologies for higher order structural analysis of biomolecules by the process of hydroxyl radical protein foot-printing. Some embodiments of the present invention relate to the determination of biopharmaceutical tertiary and quaternary structure and associated conformation using improved devices and methodologies for in vivo flash photo-oxidation of proteins within cells, tissues, or organisms to determine their higher order biomolecular structure.

Related Art

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

Biosimilars are therapeutics similar to but not identical to existing innovator or reference products. Unlike the case for small molecule drugs, biosimilars are not merely generic versions of original products. Conventional generics are considered to be therapeutically and molecularly equivalent to their originators. This is simply not the case with biosimilars, which are complex, three-dimensional biomolecules, whose heterogeneity and dependence upon production in living cells makes them quite different from classical drugs. The structures and functional activities of bio-therapeutics are exquisitely sensitive to their environments. The intended structure of a therapeutic is maintained by a delicate balance of factors, including concentration of the protein, control of post-translational modifications, pH as well as co-solutes in the formulation, and production/purification schemes (Gabrielson, J. P.; Weiss IV, W. F., *Technical decision-making with higher order structure data: starting a new dialogue*; Journal of pharmaceutical sciences, 2015). As such, biopharmaceutical structure must be prudently maintained, for if not held in check, undesirable and adverse pharmacological consequences can arise.

Adverse drug reactions (ADR) of biopharmaceuticals are typically attributed to exaggerated pharmacology as well as immunological reactions. The range of patient ADR's extends from symptomatic irritation to morbidity and death. While the etiology for some ADR's may be traced to patient pharmacogenomic sensitivity, many are attributed to intrinsic properties of the therapeutic, which has resulted in morbid and fatal patient consequences and substantial financial loss to the biotherapeutic industry (Giezen, T. J.; Schneider, C. K., *Safety assessment of biosimilars in Europe: a regulatory perspective*; Generics and Biosimilars Initiative Journal; 2014). As such, the occurrence of catastrophic ADR's has exemplified the need for improved analytics for the development and quality control of biopharmaceuticals.

In order to minimize ADR's and to facilitate the development of biosimilars, the FDA, the Center for Drug Evaluation and Research, and the Center for Biologics Evaluation and Research have issued guidelines that stress the use of state-of-the art technology for evaluating protein higher order structure (HOS) (*Quality considerations in demonstrating bio-similarity of a therapeutic protein product to a reference product; guidance for industry*; U.S. Department of Health and Human Services; Food and Drug Administration; Center for Drug Evaluation and Research; Center for Biologics Evaluation and Research Washington, D.C.; 2015). HOS analysis involves the determination of the tertiary and quaternary structure and associated conformation of a given biomolecule. Such biomolecules include protein and protein conjugates which may or may not be considered to be a biotherapeutic agent. Although a variety of HOS analytics exist today, their inadequacies to reliably predict biotherapeutic efficacy and safety has been brought into question, establishing the unmet need for new and improved HOS analytics (Gabrielson, J. P.; Weiss IV, W. F., *Technical decision-making with higher order structure data: starting a new dialogue*; Journal of pharmaceutical sciences; 2015).

A technique to address the unmet need for HOS analysis is irreversible protein hydroxylation, in combination with mass spectrometry (MS), (Hambly, D. M.; Gross, M. L., *Laser flash photolysis of hydrogen peroxide to oxidize protein solvent-accessible residues on the microsecond timescale*; Journal of the American Society for Mass Spectrometry; 2005). This process has been coined hydroxyl radical protein foot-printing (HRPF). A variety of techniques have been used to perform HRPF. Perhaps the most widely used approach relies upon fast photochemical oxidation of proteins (FPOP) that generates hydroxyl (OH) radicals from hydrogen peroxide ($H_2O_2$) using a single, high fluence, short pulse of UV light. The reaction of OH radicals and solvent exposed amino acids typically results in net insertion of one oxygen atom into the amino acid. OH radicals are short-lived, and when generated by a brief UV pulse, reactions between amino acids and radicals may be completed before any conformation change by the labeled protein can occur (Konermann, L.; Tong, X.; Pan, Y., *Protein structure and dynamics studied by mass spectrometry: H/D exchange, hydroxyl radical labeling, and related approaches*; Journal of mass spectrometry; 2008). The mass spectra of the peptide products of enzyme digestion show various levels of oxidation marked by peak shifts of 16 Da, 32 Da, 48 Da, etc. This information can be used to deduce which of the peptides are located on the exterior of the HOS and, thus, lead to greater understanding of the HOS.

A technical limitation of FPOP HRPF that deleteriously impacts comparative studies stems from the reaction of OH radicals with non-analyte components in the sample, such as buffer constituents, incipient solutes, and extraneous biologicals. Variability in the rate of background scavenging causes trial-to-trial irreproducibility, which has limited comparative studies (Niu, B. et al.; *Dosimetry determines the initial OH radical concentration in fast photochemical oxidation of proteins (FPOP)*; Journal of the American Society for Mass Spectrometry; 2015). While OH radicals are excellent probes of protein topography, they also react with many compounds found in analytical preparations. Competition between analyte protein and background scavengers for free OH radicals exists, making it desirable to measure the effective concentration of radical available to oxidize a target protein to ensure reproducible results. In photochemistry, effective radical concentration is measured using a radical dosimeter internal standard. Ideally, a dosimeter would have: a simple relationship between effective radical concentration and dosimeter response; a simple, rapid, and non-destructive measurement means; and be unreactive to most proteins.

Prior art teaches radical dosimetry as performed using spiked peptide internal standards (Niu, B., et al., *Dosimetry determines the initial OH radical concentration in fast photochemical oxidation of proteins (FPOP)*. J Am Soc Mass Spectrom, 2015. 26 (5): p. 843-6; Niu, B., et al., *Incorporation of a Reporter Peptide in FPOP Compensates for Adventitious Scavengers and Permits Time-Dependent Measurements*. J Am Soc Mass Spectrom, 2016), or a UV absorbing internal standard, such as adenine, added to the buffer and assessed in a post-labeling manner (Xie, B.; Sharp, J. S., Hydroxyl Radical Dosimetry for High Flux Hydroxyl Radical Protein Foot-printing Applications Using a Simple Optical Detection Method. *Analytical chemistry* 2015, 87 (21), 10719-23). In peptide radical dosimetry, labeled peptide and target protein are subsequently analyzed using LC-MS (with optional proteolysis) to assess the relative ratio of oxidized peptide to that of the target protein. Should the desired peptide to protein oxidation ratio not be achieved, the entire experiment is repeated adjusting the concentration of $H_2O_2$ dependent upon the need to either increase or decrease effective OH radical load. For adenine dosimetry, the effective change in adenine UV absorbance is determined upon completion of the labeling process, and the ratio of the achieved vs target adenine UV absorbance change is determined. The $H_2O_2$ concentration is subsequently varied in accordance with the desired change in UV absorbance. Both of these approaches are performed after labeling has been completed and do not enable real-time adjustment of effective OH radical load, consuming precious sample and needlessly wasting investigator time.

U.S. Provisional application 62/511,571 and International Application PCT/US18/34682 teach systems and methods by which to perform radical dosimetry in real-time, as biologicals are labeled during the FPOP HRPF process. While creating a real-time means to adjust and compensate for variation in background scavenging, the systems and method taught in these applications requires the addition of an extrinsic internal standard dosimeter to the biological mixture. Under some conditions, the extrinsic internal standard may cause artifactual changes in biomolecular higher order structure, and as such, be incompatible for the desired goal of providing a facile means of characterizing nascent higher order structure of biologicals. The disclosures of the 62/511,571 and PCT/US18/34682 applications are hereby incorporated herein by reference.

U.S. Provisional application Ser. No. 62/747,247 describes a device and methodologies by which commonly used biological buffer systems can be employed as radical dosimeter internal standards. The photometric properties of some commonly employed biological buffers are altered in a predictable manner upon OH radical attack. As such, these buffers can be employed as radical dosimeter internal standards, eliminating the need to add extrinsic reagents, and as the solvating properties of these buffers are well established to stabilize nascent configurations of biomolecules, they do not alter biological higher order structure.

The afore noted art describes devices and means by which to perform HRPF radical dosimetry while labeling proteins or biopharmaceuticals in vitro. However, the practice of applying the results of in vitro structural experiments to authentic in vivo behavior has been brought into question (Mourao, M. A.; Hakim, J. B.; Schnell, S., Connecting the dots: the effects of macromolecular crowding on cell physiology. *Biophysical Journal* 2014, 107 (12), 2761-2766). Because of shortcomings of in vitro HRPF, there has been recent interest and desire to extend the use of HRPF to intact whole cells in an in vivo manner. For example, US Patent Application Publication US 2018/0079998 describes a means and methodology by which in vivo HRPF can be performed. Briefly, a plurality of fused-silica capillary tubes and microfluidic fittings are used to support the mixing of buffer suspended cells with $H_2O_2$. As taught, $H_2O_2$ is rapidly taken up by the cells without causing cellular disruption, inducing apoptosis, or precipitating cell death. However, the systems and methods taught still result in a variety of shortcomings.

SUMMARY

Various embodiments of the invention include systems and methods that addresses the above noted shortcomings of present day in vitro HRPF by providing the means for real-time, in vivo measurement of effective hydroxyl radical concentration and adjustment for unwanted background scavenging using the photometric properties of an in vivo radical dosimeter internal standard; the means by which cellular singulation and partitioning can be assessed and reproducibly controlled; as well as a means to determine the arrival time of a cell into an HRPF photolysis zone.

Various embodiments of the invention are directed to systems and methods for the analysis of protein higher order structure comprising improved embodiments to perform in-vivo flash photo-oxidation of proteins enabling advanced hydroxyl radical protein foot-printing. In some embodiments this invention provides an in-line, in vivo radical dosimetry system wherein closed-loop control is established between the flash photolysis system and dosimeter to control irradiance of the flash photolysis system in response to measured changes in the photometric properties of an intra-cellular, internal standard radical dosimeter.

In some embodiments, the invention includes an in-line, in vivo radical dosimetry system wherein closed-loop control is established between an automated, in-line microfluidic mixing system and dosimeter to control the concentration of $H_2O_2$ in response to measured changes in the photometric properties of an intra-cellular, internal standard radical dosimeter.

In some embodiments, the invention includes an in-line, in vivo radical dosimetry system wherein closed-loop control is established between the flash photolysis system and dosimeter to control irradiance of the flash photolysis system in response to measured changes in the photometric properties of an intracellular internal standard radical dosimeter, for which OH radicals are created by the photolysis of intracellular $H_2O_2$.

In some embodiments, the invention includes an in-line, in vivo radical dosimetry system wherein closed-loop control is established between the flash photolysis system and dosimeter to control irradiance of the flash photolysis system in response to measured changes in the photometric properties of an intracellular internal standard radical dosimeter, for which OH radicals are created from water using photo-catalytic metal oxides, external of the cell.

In some embodiments, the invention includes an in-line, in vivo radical dosimetry system wherein closed-loop control is established between the flash photolysis system and dosimeter to control irradiance of the flash photolysis system in response to measured changes in the photometric properties of an intracellular internal standard radical dosimeter, for which OH radicals are created from water using photo-catalytic metal oxides, internal to the cell.

In some embodiments, using an in vivo, in-line radical dosimetry system, the invention includes methods of producing labeled biomolecules for analysis comprising: (1) mixing cells with a biological buffer, internal standard radical dosimeter that is ultimately taken up by the cell, and other required labeling reagents, (2) introducing said cells into an optical dosimetry zone, (3) determining the nascent photometric properties of said cells, (4) photo-irradiating said cells in an optical photolysis zone with at least one burst of UV irradiation, (5) determining the change in photometric properties for said cells after photo-irradiation, and (6) adjusting the spectral irradiance of the UV source light in accordance with the change in radical dosimeter photometric property.

In some embodiments, using an in vivo, in-line radical dosimetry system, this invention includes methods of producing labeled biomolecules for analysis comprising: (1) mixing cells with a biological buffer, internal standard radical dosimeter that is ultimately taken up by the cell, and other required labeling reagents, (2) introducing said cells into an optical dosimetry zone, (3) determining the nascent photometric properties of said cells, (4) photo-irradiating said cells within an optical photolysis zone with at least one burst of UV irradiation, (5) determining the change in photometric properties for said cells after photo-irradiation, and (6) adjusting the concentration of $H_2O_2$ using an in-line, microfluidic mixer in accordance with the change in radical dosimeter photometric property.

In some embodiments, using an in vivo, in-line radical dosimetry system, the invention includes methods of producing labeled biomolecules for analysis comprising: (1) mixing said cells with a biological buffer, internal standard radical dosimeter that is ultimately taken up by the cells, and metal-oxide photo-catalyst, (2) introducing said cells into an optical dosimetry zone, (3) determining the nascent photometric properties of said cells, (4) photo-irradiating said cells in an optical photolysis zone with at least one burst of UV irradiation, (5) determining the change in photometric properties of said cells after photo-irradiation, and (6) adjusting the spectral irradiance of the UV source light in accordance with the change in radical dosimeter photometric property.

In some embodiments, using an in vivo, in-line radical dosimetry system, the invention includes methods of producing labeled biomolecules for analysis comprising: (1) mixing cells with a biological buffer and internal standard radical dosimeter that is ultimately taken up by the cell, (2) introducing said cells into an optical dosimetry zone, (3) detecting the arrival and presence of said cells cell by monitoring the intensity of scattered light exiting the dosimetry zone, (4) determining the elapsed time between the arrival of consecutive cells, (5) determining the cell isolation volume per the product of the elapsed time and net buffer flow rate, and (6) adjusting the sheath flow and buffer flow parameters to achieve a desired cell isolation volume.

In some embodiments, using an in vivo, in-line radical dosimetry system, the invention includes methods of producing labeled biomolecules for analysis comprising: (1) mixing cells with a biological buffer and internal standard radical dosimeter that is ultimately taken up by the cell, (2) introducing said cells into an optical dosimetry zone, (3) detecting the arrival and presence of a cell by monitoring the intensity of scattered light exiting the dosimetry zone, (4) determining the net flow rate for said arriving cell, (5) determining the interconnect volume that extends from the photolysis zone and the dosimetry zone, (6) determining the transit time required for said cell to travel from the photolysis zone to the dosimetry zone, (7) determining the photolysis zone arrival time for said cell, and (8) triggering the photolysis system at such time when all subsequent cells arrive at the photolysis zone.

Following the production of labeled biomolecules other methods, such as mass spectrometry or electrophoresis, may be used to identify labeled peptides and deduce information regarding higher order structures of biomolecules in vivo.

Various embodiments of the invention include an analysis system comprising: a sample introduction system configured to provide intact biological entities to a photolysis zone, the biological entities being isolated from each other in a focused sheath flow; a photolysis light source configured to generate light to generate hydroxide radicals from a source of hydroxide radicals; a photolysis zone configured to receive the sheath flow and the light so as to oxidize an internal standard and so as to oxidize biological compounds of the biological entities in vivo; a dosimetry zone configured to receive the biological entities from the photolysis zone, to detect presence of the biological entities using a scattered light detector and to detect oxidation of the internal standard using a fluorescence detector; control logic configured to determine that a target concentration of hydroxide radicals was generated for each of the biological entities and to adjust operation of the photolysis zone to meet the target concentration of hydroxide radicals; and a reservoir configured to receive the biological entities including the oxidized biological compounds.

Various embodiments of the invention include a method of oxidizing biomolecules within an intact cell, the method comprising: introducing a sample mixture containing at least one cell into a photolysis zone, a source of hydroxide radicals and a dosimeter internal standard into a photolysis zone of a flash photolysis system; providing light to generate the hydroxide radicals from the source of hydroxide radicals, the hydroxide radicals being configured to oxidize biomolecules within the at least one cell; waiting an optionally predetermined time for the at least one cell to reach a dosimetry zone of a radical dosimeter configured to detect a photometric property of the dosimeter internal standard resulting from reaction of the dosimeter internal standard and the hydroxide radicals, wherein the at least one cell is detectable within a dosimetry zone of the radical dosimeter by light scattering; measuring a photometric property of the dosimeter internal standard using the radical dosimeter, while the at least once cell is within the dosimetry zone; determining that a target level of hydroxide radicals was not generated based on the measured photometric property of the dosimeter internal standard; and adjusting a concentration of hydroxide radicals within the photolysis zone by adjusting at least one of: 1) an amount of light provided to the photolysis zone, 2) a concentration of the source of hydroxide radicals, 3) a flow rate of the at least once cell within the photolysis zone, or 4) adjusting a time of providing the light to the photolysis zone.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized. Further, the above objects and advantages of the invention will become readily apparent to those skilled in the art from reading the following description of exemplary embodiments when considered in the light of the accompanying figures that incorporate features of the present invention. The components in the drawings are not necessarily to scale, emphasis instead being placed upon clearly illustrating the principles of the present disclosure.

Any of the methods described herein can according to specific embodiments further make use of any one or more of the following of which.

DETAILED DESCRIPTION

Figure 1:
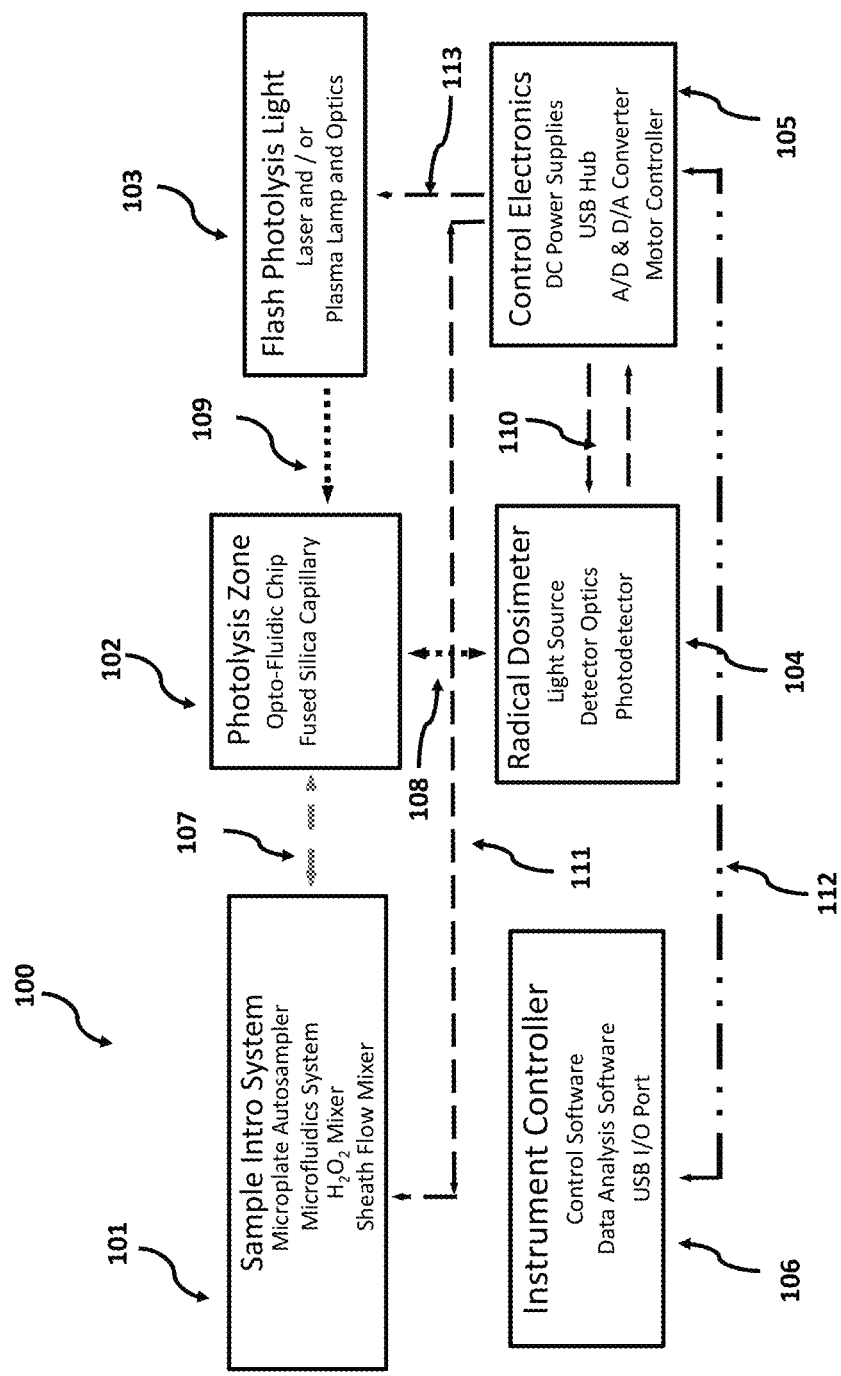
FIG. 1 illustrates embodiments of a flash photolysis system 100, configured for with real-time radical dosimetry and comprising of a number of subassemblies. Shown are: sample introduction system 101; photolysis zone 102; flash photolysis light 103; radical dosimeter 104; control electronics 105; instrument controller 106; fluidic inter-connection line 107 between the sample introduction system 101 and photolysis zone 102; fluidic inter-connection line 108 between the photolysis cell and radical dosimeter; photonic interconnect 109 between flash photolysis system 103 and photolysis zone 102; electronic inter-connects 110 between the radical dosimeter 104 and control electronics 105; electronic inter-connects 111 between the sample introduction system 101 and control electronics 105; electronic inter-connects 112 between the control electronics 105 and instrument controller 106; and electronic inter-connects 113 between the control electronics and flash photolysis system. Together, photolysis zone 102, flash photolysis light 103 and radical dosimeter 104 comprise a "flash photolysis system." Photolysis zone 102 is typically included in a photolysis cell.

Devices and methods are provided for the analysis of biomolecular higher order structure that is accomplished by selective labeling of solvent exposed molecular groups, as catalyzed by in vivo fast photo-oxidation with real-time monitoring and control of effective OH radical concentration. Moreover, devices and methods are provided for the analysis of biomolecular higher order structure that is accomplished by in vivo fast photo-oxidation with real-time monitoring and control of in vivo species isolation volume and subsequent flash photolysis. The devices and methods can be applicable to a variety of in vivo embodiments that are photometrically translucent or transparent such as but not limited to: eukaryotic cells, prokaryotic cells, bacteria, intra-cellular viruses, virions, virus-like particles, single-cell organisms, eukaryotic tissues, and multi-cellular organisms. While the present invention refers to cells for illustrative purposes, such reference is not restrictive, and it is understood that such references are inherently applicable to any and all photometrically translucent or transparent in vivo biological or non-biological entities.

The devices and methods can be applicable to a variety of research fields, such as: general protein biochemistry; diagnostics research; infectious disease research; biopharmaceutical research and development; antibody research and development; biosimilar development; therapeutic antibody research and development; small molecule drug research and development; and development of other therapeutic compounds and materials. Moreover, the devices and methods can be applicable to a variety of research analyses such as: protein-ligand interaction analysis; protein-protein interaction analysis; protein-DNA interactions; protein-RNA interactions; protein-fusion product analysis; protein conformation and conformational change analysis; cell-cell interactions; virus-cell interactions; small drug molecule mode of action analysis; biopharmaceutical mode of action analysis; antibody-antigen analysis; protein epitope mapping; protein paratope mapping; and chemical reaction monitoring.

The device can receive cells for subsequent chemical labeling via a step-wise introduction of cells by manually pipetting the cells into appropriate micro-centrifuge tubes or microplates that are placed into the system's sample introduction assembly. Alternatively, the device can be hyphenated with and receive cells directly from other separation and analysis instruments such as but not limited those which perform selective cell sorting, cell counting, and cell isolation from tissue.

This section provides a general overview of the flash photolysis instrument with in-line, in vivo radical dosimeter that uses the photometric properties of an internal standard dosimeter to assess and ultimately control in vivo effective OH radical concentration. Moreover, this section provides a general overview of the present invention that uses the photometric properties of an in vivo embodiment to assess isolation volume and to control precise triggering of the flash photolysis system at such time when the in vivo embodiment arrives at the system's photolysis zone. A detailed description of each sub-assembly is provided elsewhere herein. Moreover, methods that describe the interplay of these subassemblies are provided to enable understanding of typical instrument operation.

Various embodiments of the invention include a flash photolysis system 100, as illustrated in FIG. 1. Flash photolysis system 100 is configured to oxidize sample cells in real-time to achieve in vivo radical dosimetry. In vivo analytes (i.e. cells) are introduced via the sample introduction system 101. Cells in suspension can be presented using small volume micro-centrifuge tubes or by using multi-well microtiter plates as readily available from Eppendorf (Hamburg, Germany) Microfluidic circuitry is configured for cellular aspiration, mixing with $H_2O_2$, cellular hydrodynamic focusing using a sheath flow apparatus, transportation to photolysis and dosimetry zones, as well as the transportation and deposition of labeled cells. In some embodiments, sample introduction system 101 is configured to provide intact biological entities to a photolysis zone (e.g., photolysis zone 102, the biological entities being isolated from each other in a focused sheath flow. The sheath flow is typically configured to isolate the biological entities from each other. For example using proper conditions, the biological entities are separated from each other by regular intervals.

Photo-oxidation occurs within the photolysis zone 102. In some embodiments, a photolysis zone 102 is comprised of a fused silica capillary as available from Polymicro Technologies—Molex (Phoenix, AZ, USA). Typical capillary internal diameter can range from 50 micrometers to 5 mm Typical wall thickness can range from 50-2000 micrometers. In some embodiments, opto-fluidic chips are fabricated using a variety of techniques such as lithography assisted wet chemical etching, dry reactive ion etching, and laser ablation micro-structuring that create microfluidic channels within a quartz substrate. In some embodiments, opto-fluidic chips are fabricated by embossing fluidic channels within a plastic substrate, where formed fluidic channels transport sample into optically transparent cells created by sealing optically transparent windows to regions where the plastic substrate has been removed. Exemplary plastic substrates include but are not limited to: polycarbonate, polyethylene, polyether-ether-ketone, cyclic olefin polymer, cyclic olefin copolymer, polytetrafluorethene, Kalrez®, and polychlorotrifluoroethylene. Fluidic and optical channel internal diameters can range from but are not limited to 0.1 to 5.0 mm. In some embodiments, fluidic and optical channels can have different internal diameters to ideally match disparate requirements of fluid transfer, fluid mixing, hydrodynamic focusing, and optical coupling. Moreover, the opto-fluidic chip can contain an optical wave-guiding structure, such as an integral optical fiber, monolithic waveguide, liquid core waveguide, or evanescent guiding means using metal oxides, rare-earth metals, or grating structures. In another embodiment at least one sample contacting surface of the photolysis cell is coated with a photocatalytic metal oxide, such as $TiO_2$. For some photocatalytic metal-oxide formulations, photolysis can be initiated using long UV (wavelength≥300 nm) or visible light. For these embodiments, capillaries and opto-fluidic chips can be fabricated using various varieties of glass, such as BK-7 or Borofloat® 33 (Schott AG, Germany), in lieu of fused silica or quartz. In another embodiment, quartz or glass opto-fluidic cells comprise a resonance structure to support resonance and/or multi-pass incident photon collision with suspended cells, dissolved reactants, such as but not limited to $H_2O_2$, suspended metal-oxide nanoparticles, or immobilized metal oxide films upon at least one sample contacting surface.

The photolysis zone 102 receives suspended cells from the sample introduction system 101 via a microfluidic path 107. After processing, photo-irradiated cells within the photolysis zone 102 are transferred into the radical dosimeter 104. The photolysis zone 102 is in optical communication with the flash photolysis light 103. Flash photolysis light 103 is an example of a photolysis light source configured to generate light to generate hydroxide radicals within photolysis zone 102 from a source of hydroxide radicals. In some embodiments, photolysis zone 102 is configured to receive the sheath flow including biological entities, to receive the light from flash photolysis light 103 so as to oxidize the dosimeter internal standard so as to oxidize biological compounds of the biological entities in vivo. For example, peptides comprising amino acids may be oxidized in the photolysis zone 102.

The photolysis zone 102, flash photolysis light 103 and radical dosimeter 104 comprise a flash photolysis system. The flash photolysis system is comprised of: a plasma flash lamp or other appropriate light source such as an excimer laser, a solid state laser, or laser diode; and associated light collection/transmission optics to match the requirements of the light transmission means to the photolysis zone.

The radical dosimeter 104 is configured to receive fluid and suspended cells from the photolysis zone 102, or in alternative embodiments, the radical dosimeter 104 is incorporated into the photolysis zone 102 by employing an orthogonal optical path. A variety of photometric detection schemes may be employed by the radical dosimeter to monitor the associated photometric properties of the dosimeter internal standard. In some embodiments, the dosimeter internal standard can be an extraneous additive that is spiked into the biological sample. In some embodiments, the intrinsic photometric properties of a biological buffer system, once taken up by the cell, may serve as an intrinsic dosimeter internal standard. By "intrinsic" or "intrinsic to a buffer" it is meant that the internal standard is one of the chemical species that provides the buffering property. The buffer is optionally a physiologically compatible buffer configured to maintain the cells at a physiological pH or ion concentration. In some embodiments, the internal standard is configured to become fluorescent as a result of the light received from flash photolysis light received in photolysis zone 102. For example, the dosimeter internal standard may increase fluorescence by factors of at least 10, 100 or 1000 times upon reaction with hydroxide radical, in various embodiments.

Photometric detection schemes include but are not limited to: fluorescence, photometric absorbance, refractive index detection, light scatter detection, and luminescence. In some embodiments, the photometric detection scheme comprises a fluorescence detector employing ultra violet (UV) photo-excitation source to create UV fluorescence or emission. In some embodiments, the fluorescence detector employs a UV excitation source to create visible fluorescence or emission. In some embodiments, the fluorescence detector employs a visible excitation source to create visible fluorescence or emission. In some embodiments, the fluorescence detector also includes an integral light scatter detector.

The control electronics 105 functions to: provide direct current (DC) drive voltage, derived from laboratory alternating current (AC) power sources, to peripheral assemblies; provide analog and digital control signals to peripheral devices; receive analog or digital information from peripheral devices; provide ADC and digital to analog conversion (DAC) functions; and provide data to and receive commands from the instrument controller 106. In a typical embodiment, the control electronics assembly comprises a motor controller that interfaces with motors located within the sample introduction-collection system 101. Moreover, the control electronics assembly in such embodiments may contain a universal serial bus (USB) hub for digital communication with the instrument controller 106.

The instrument controller 106 functions to provide process control for various instrument peripheral devices while receiving status and data information from these devices in digital format. In some embodiments, the instrument controller 106 runs a software control program with two main modules: a low level, multi-threaded module for instrument component control and a high level user interface (UI) module. In some embodiments, the control electronics 105 comprises an embedded microprocessor that provides low level instrument component control while communicating with a high level UI control program of the instrument 106 via a USB or wireless interface.

Together instrument controller 106, control electronics 105 and various interconnections represent control logic configured to control flash photolysis system 100. This control logic can be configured to perform steps of any of the methods disclosed herein. For example, in some embodiments, control logic is configured to determine that a target concentration of hydroxide radicals was generated for each biological entity. This target concentration is optionally selected to assure that that an oxidation reaction of cell constituents has sufficient oxidizing agent to go near a desired level of completion.

The control logic may further be configured to manage the feedback loop that includes adjusting conditions in the photolysis zone 102 to meet the target concentration of hydroxide radicals. The conditions in the photolysis zone 102 may be adjusted by, for example, changing a concentration of a source of hydroxide radicals, changing a flow rate in the sample introduction system 101, changing an amount of light received from the photolysis light source 103, changing a time at which the light is received from the photolysis light source, changing a separation distance/volume of isolated cells, and/or the like. By changing conditions in the photolysis zone 102, control logic can provide feedback to sample introduction system 101 and/or the photolysis light source 103 based on analysis of a first cell to improve analysis of a second cell.

In some embodiments, control logic is configured to normalize a quantitation of oxidized and/or identified peptides from a cell based on a fluorescence signal from the internal standard within the dosimetry zone 210. This allows comparison of results from different experiments using different instances of flash photolysis system 100.

The control logic is optionally further configured to determine a time the photolysis light is received by cells in the photolysis zone 102 and/or to determine a time period between which isolated cells enter the photolysis zone 102. These determinations may be based on detection of fluorescence and/or scattered light in the dosimetry zone 210 and may be controlled by adjusting flow rates and/or volumes in sample introduction system 101.

The control logic is optionally further configured to control flow of cells to labeled cell reservoir 211 and analyzer 212. For example, the control logic may be configured to control flow of cells such that ruptured cells are diverted from a particular container of labeled cell reservoir 211, or such that different oxidized cells are placed in different compartments over a function of time. In some embodiments, control logic is configured to use an analyte signal from analyzer 212 to control any aspect of flash photolysis system 100.

Instrument controller 106 and control electronics 105 are optionally combined into a single device.

Figure 2:
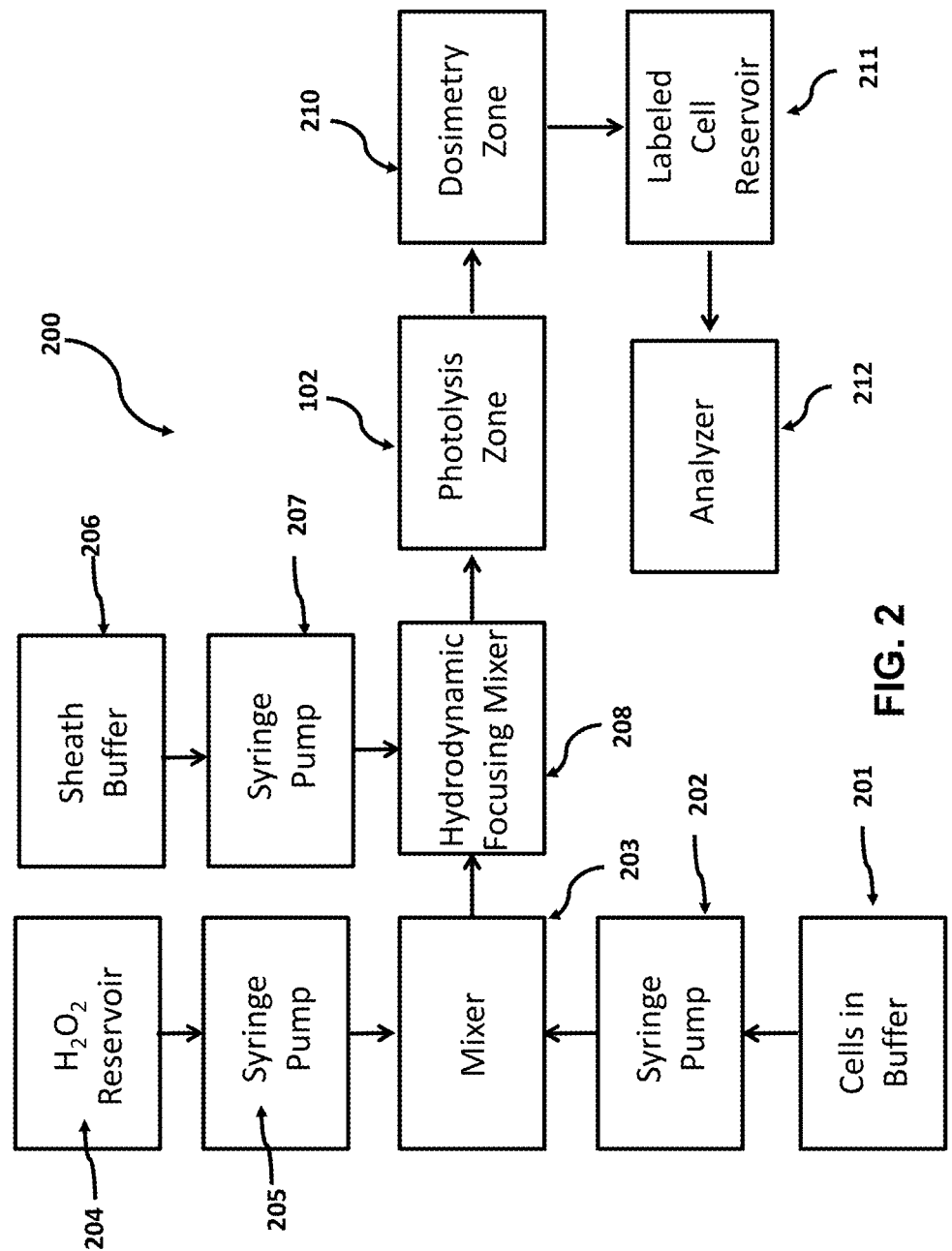
FIG. 2 illustrates movement of sample between various elements of the flash photolysis system 100 illustrated in FIG. 1, according to various embodiments. The sample movement includes cell introduction, sample processing, and labeled cell collection. Shown are: cells as suspended in running buffer 201; cell suspension syringe pump 202; microfluidic mixer 203; hydrogen peroxide reservoir 204; hydrogen peroxide syringe pump 205; sheath buffer reservoir 206; sheath buffer syringe pump 207; hydrodynamic focusing mixer 208; photolysis zone 209; dosimetry zone 210; labeled cell reservoir 211; and analyzer 212.

FIG. 2 illustrates further details of the flash photolysis system 100 of FIG. 1. Flash photolysis system 100 is used for cell introduction, cell processing, and processed cell collection. Cells to be processed are suspended/placed in buffer and stored in reservoir 201. In some embodiments the cells have been previously incubated with a buffer containing an extrinsic and/or intrinsic radical dosimeter internal standard. This incubation allows the internal standard to enter the interior (absorbed) and/or be adsorbed onto the surface of the cells. In some embodiments, the buffer includes compounds that act inherently as an intrinsic in vivo internal standard to perform radical dosimetry. Under microprocessor control (e.g., control electronics 105 and/or Instrument controller 106, syringe pump 202 aspirates cells from reservoir 201 and pumps them into mixer 203. The elements 201-208 and 211 are optionally part of sample introduction system 101.

$H_2O_2$ is stored in reservoir 204. Under microprocessor control, syringe pump 205 aspirates $H_2O_2$ from reservoir 204 and pumps the aspirated $H_2O_2$ into mixer 203. The aqueous concentration of $H_2O_2$ in reservoir 204 is selected so that at the desired net flow rate for pumps 202 and 205 and the effective desired final concentration of $H_2O_2$ are achieved. Exemplary $H_2O_2$ concentration range from, but are not restricted to, 5-200 mM. Exemplary net flow rates after mixer 203 range from, but are not restricted to, 5-100 uL/min. $H_2O_2$ is an example of a source of hydroxide radicals, which is added to the cells (or other biological entities) by sample introduction system 101.

Sheath buffer is stored in reservoir 206. Under microprocessor control, syringe pump 207 aspirates sheath buffer from reservoir 206 and pumps the sheath buffer into hydrodynamic focusing mixer 208. Cells mixed with $H_2O_2$ are pumped from mixer 203 into the hydrodynamic focusing mixer 208 by the combined pumping action of pumps 202 and 205. Subsequently, sheath buffer functions to hydrodynamically focus the cells, creating a single-file array of cells, each isolated by a given volume of sheath buffer. The single-file array of cells is created by constricting the flow from mixer 203 to the extent that a diameter of the flow is similar to the diameter of the cells. Exemplary sheath buffer flow rates range from, but are not restricted to, 20-1000 uL/min.

After single-file cell isolation, by the combined pumping of syringe pumps 202, 205, and 207, cells are shuttled into photolysis zone 102, where they may be irradiated by the flash photolysis light 103. After flowing through the photolysis zone 102, cells can be pumped into the dosimetry zone 210 which is part of radical dosimeter 104, wherein photometric properties of the cells can be measured. Dosimetry zone 210 is configured to detect oxidation of the internal standard using, for example, a fluorescence detector. Dosimetry zone 210 is optionally also configured to detect presence of the cells (or other entities) within the dosimetry zone 210 using a detector configured to detect light scattering. This scattered light detector is optionally also configured to determine if the cell is intact. For example, the scattered light detector and associated instrument control logic may be configured to distinguish between cells that are intact, cells that are disrupted, and cells that are stuck together. In some embodiments, radical dosimeter 104 includes both dosimetry zone 210 and photolysis zone 102. Dosimetry zone 210 includes photolysis zone 102. The photometric properties measured can include, but are not restricted to, photometric fluorescence and/or photometric absorbance. After leaving the dosimetry zone 210, suspended cells are optionally pumped into and collected in a labeled cell reservoir 211. Real-time measurements made in Dosimetry zone 210 allow for a feedback loop in which photolysis conditions can be modified to assure that a desired amount of $H_2O_2$ production occurs and a desired amount of in vitro or in vivo analyte oxidation.

During initial operation of the system, a base-line measurement of the cell's photometric property is optionally taken. The baseline measurement is performed for the introduced cell without any photolysis. Once the baseline measurement is made, photolysis proceeds and once the (one or more) photo-exposed cells enter the dosimetry zone, the photometric property of the photo-exposed cells are assessed. In some embodiments, labeled cell reservoir 211 contains more than one fluid storage compartment. For example, labeled cell reservoir 221 may include several compartments or wells in which oxidized biological compounds may be selectively placed. In some embodiments, different aliquots of the output of dosimetry zone are placed in different compartments based on fluorescence and/or light scattering measurements made in dosimetry zone 210. In one compartment, non-photo-exposed cells that flowed through the system during the baseline measurement process are collected. In another compartment, photo-exposed intact cells are collected. In another compartment cells that were found not to be intact may be placed. Photo-exposed (e.g., oxidized cells) may be placed in different compartments as a function of time in order to perform time-based experiments, such as kinetic studies. The compartments may be "sample wells," lengths of capillary, channels, and/or the like.

From labeled cell reservoir 211 collected samples are optionally analyzed using analyzer 212. Analyzer 212 is configured to perform chemical analysis of the samples. For example, Analyzer 212 may be configured to identify peptides, carbohydrates, metals, nucleic acids, lipids, and/or amino acids oxidized in the photolysis zone 102. Analyzer 212 may include, for example, a mass spectrometer, scintillator, electrophoresis device, chromatograph, and/or any other device configured to separate and/or identify sample constituents based on radioactivity, mass, charge, size, or other chemical property. In some embodiments, analyzer 212 is configured to detect isotopic or radio isotopic labels within cells or other biological entities and optionally to identify if the components including such labels have been oxidized. In some embodiments, analyzer 212 is configured to measure a ratio of oxidized/non-oxidized concentrations of a particular component. In some embodiments, analyzer 212 is "in-line" with labeled cell reservoir 211 and thus configured to receive and analyze samples in real-time. For example, labeled cell reservoir 211 may include a capillary configured to provide sample directly to an input of a mass spectrometer.

Figure 3:
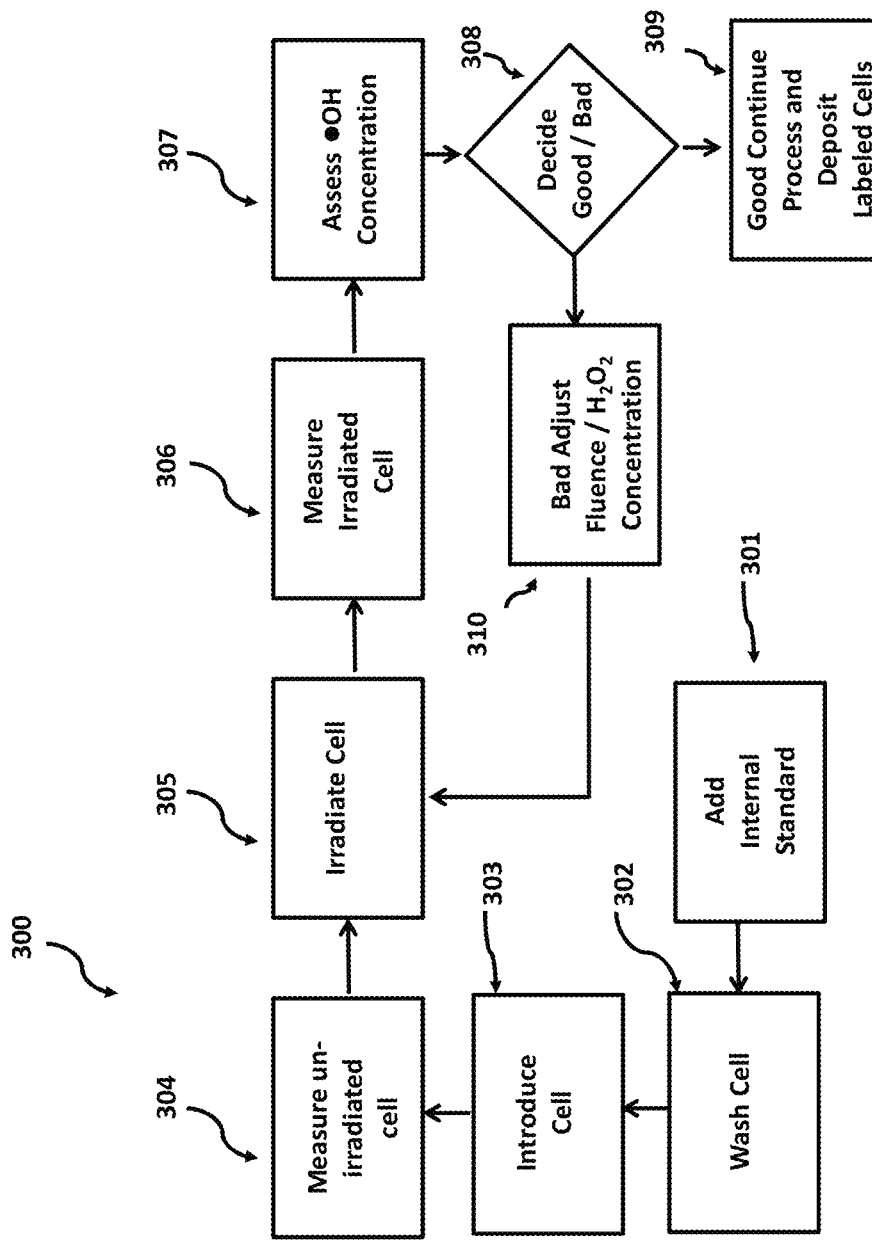
FIG. 3 illustrates methods 300 for in vivo cell labeling, according to various embodiments of the invention. Shown are: an add internal standard step 301; a wash cell step 302; an introduce step 303 including introduction of (one or more) cells to be labeled; a measure step 304 including photometric measurement of the non-irradiated cell; an irradiate step 305 including irradiation of the cell to initiate the in vivo labeling process; a measure step 306 including photometric measurement of the irradiated cell; an assess step 307 including assessment of the effective OH radical concentration by analyzing the change in the sample's photometric property after irradiation; a decision step 308 including a decision as to how the labeled cell is subsequently handled after achieving desired effective OH radical concentration; a good result step 309 including further processing of the cell based on a desired level of effective of OH radical concentration; or alternatively an adjust step 310 including adjustment of irradiation conditions for subsequent cells. Adjust step 310 results in irradiation of one or more additional cells after adjusting flash spectral irradiance and/or $H_2O_2$ concentration.

FIG. 3 illustrates methods 300 for in vivo cell labeling, according to various embodiments of the invention.

In an optional add internal standard step 301, the dosimeter internal standard is added to the cells or other entities to be analyzed. The internal standard may be intrinsic to a buffer with which the cells are mixed or added. The cells may be left in contact with the internal standard for a time such that the internal standard has time to be absorbed into the interior of the cells and/or be adsorbed on to surfaces of the cells. After this time the internal standard may be washed from the cells in a wash cells step 302. Steps 301 and 302 leave the internal standard that was absorbed in or adsorbed to the cells, while leaving the surrounding fluid practically devoid of internal standard. These two steps improve the accuracy of the measurement of the internal standard by reducing the background of internal standard not bound to the cells. Step 301 is optional where, for example, the cells already include a dosimeter internal standard.

In introduce step 303 one or more first cells are introduced into the flash photolysis system using sample introduction system 101. As noted elsewhere, the introduced cells may have added a dosimeter internal standard. For example, the cells may have been placed in a buffer including an intrinsic internal standard that we adsorbed onto a surface of the cells or absorbed into the interior of the cells. After the cells have received the internal standard, they may then be placed in a solution having minimal constituents capable of being oxidized by $H_2O_2$. This results in the internal standard being associated with the cells but not the surrounding solution.

In an optional measure step 304, the first introduced cell(s) containing intrinsic or extrinsic dosimeter internal standard are measured in an un-irradiated state (i.e., not yet oxidized using photolysis) to assess their nascent photometric properties. This initial assessment serves as the baseline measurement against which subsequent photometric property measurements can be compared.

In an irradiate step 305, an introduced cell (or cells) is irradiated in the photolysis zone 102. The irradiated cell can be the first introduced cell or a second introduced cell. In a measure step 306 one or more photometric properties of the irradiated cell(s) are measured using radical dosimeter 104. The measurements made in step 306 can be compared with those made in step 304 to determine an effective $H_2O_2$ concentration and an extent to which photolysis induced oxidation of biomolecules has occurred. In embodiments where the dosimeter internal standard is primarily associated (absorbed & adsorbed) with the cells, the measured photolysis induced oxidation represents a quantitative measurement of in vivo oxidation of the biomolecules of the cells.

In assess step 307, the measured changes in photometric properties are used as a surrogate to access the effective OH radical concentration and thereby the completeness of oxidation reactions with target (in vivo) biomolecules. In a decision step 308, it is determined if a target OH radical concentration has been achieved. If the determination is TRUE, then the method proceeds to good result step 309 in which the photolysis conditions are considered satisfactory, the oxidation process is continued on additional cells and subsequent irradiated cells are ultimately collected and analyzed as illustrated in FIG. 2. Good result step 309 optionally includes analysis of the cells using analyzer 212 and use of results from analyzer 212 to determine properties of the cells, such as kinetics, three-dimensional protein structure, molecular interaction cites, and/or the like. If the determination is FALSE, then the method proceeds to adjust step 310 in which photolysis system fluence and/or $H_2O_2$ concentration is varied and the method of FIG. 3 is repeated for additional cells to assess the new level of OH radical yield resulting from the adjusted parameters. In some embodiments the method 300 is manually operated by a user. In some embodiments, all or part of the method 300 is automated under microprocessor control using instrument controller 106 or control electronics 105. The method may be repeated until a desired level of OH radical yield and/or biomolecule oxidation is achieved. Measure step 304 may or may not be performed for every cycle of the method.

Various embodiments of the invention include in vivo Radical Dosimetry Using Intracellular Fluorescent Indicators of Oxidative Reactions. A technical limitation of fast photochemical oxidation of proteins (FPOP) hydroxy radical protein foot-printing (HRPF) arises from the reaction of OH radicals with background or non-analyte components in the sample, such as buffer constituents, extraneous proteins, cellular structures, and incipient solutes. Variability in the degree of background scavenging causes trial-to-trial irreproducibility, which has limited comparative studies (Niu, B. et al.; *Dosimetry determines the initial OH radical concentration in fast photochemical oxidation of proteins (FPOP)*; Journal of the American Society for Mass Spectrometry; 2015). While OH radicals are excellent probes of protein topography, they also react with many compounds found in analytical preparations. Competition between target protein and background scavengers for free OH radicals exists. As such, to obtain reproducible results it is desirable to measure the effective concentration of available hydroxyl radical to oxidize the target protein or proteins and to accordingly adjust total hydroxyl radical production. For in vivo HRPF, radical dosimetry is optionally performed by monitoring only changes in effective OH radical load that occur within the cell, and in some cases preferentially occur within specific cellular organelles.

In photochemistry, effective radical concentration is measured using a radical dosimeter, such as radical dosimeter 104. Ideally, a dosimeter would have: a simple relationship between effective radical concentration and dosimeter response; a simple, rapid, and non-destructive measurement means; and be unreactive to most proteins. In one approach the use of radical dosimetry for the assessment of background scavenging for in vitro systems includes methods of determining free OH radical concentration by measuring the absorbance change of adenine. This approach includes an off-line method of collecting photo-exposed adenine and associated analyte protein, where flow is diverted from a capillary photolysis cell and is directed to an off-line UV detector. This approach consumes substantial product (several microliters) and requires much time to generate sufficient volume to transport the sample and to perform UV absorbance measurements. Other approaches include methods to perform in vitro radical dosimetry in real-time, as biologicals are labeled during the FPOP HRPF process. In these approaches, a photometric detection scheme is applied to the flowing stream of analyte in order to detect changes in the optical properties of a dosimeter internal standard. Particular description is given to the use of adenine as a dosimeter internal standard that is added to the analytical sample as an exogenous or extrinsic component. Moreover, these approaches include methods in which labeling parameters may be altered in real-time to achieve desired levels of effective OH radical concentration and associated labeling efficiency, and methods by which effective OH radical yield can be controlled by varying the fluence and/or spectral irradiance of a plasma flash lamp source in addition to dithering $H_2O_2$ concentration. See, for example, US Pat. Pub. 2014/0030751, U.S. Provisional application 62/511,571 and International Application PCT/US18/34682.

While the above approaches teach in vitro methods by which to perform off-line and in-line closed loop radical dosimetry to improve the reproducibility of in vitro HRPF, they fail to address the requirements for in vivo HRPF. For in vivo HRPF to be effective, each cell are preferably photo-irradiated only once with a short burst of UV irradiation, employing typical pulse widths on the order of 10-20,000 nanoseconds. Further, for in-line, in vivo radical dosimetry to be most useful, photometric measurements should be taken in a way such that a single cell or a given quantity of cells are consistently probed to enable comparative measurements. As such, a flowing stream of cells should be created in a precise manner that provides a predictable amount of isolation volume that segregates each cell in its single-file array, and enables precise and predictable temporal delivery of each cell, or a given number of cells, to photolysis and dosimetry zones. It is also desirable to separate, for both measurement and collection, those cells that have been irradiated from those that have not.

In vivo HRPF greatly benefits from the assessment of the effective intracellular OH radical concentration. Accordingly, in vivo radical dosimetry benefits when a dosimeter internal standard (intrinsic or extrinsic) only (or predominantly) present within the cell and not in the extracellular fluid. Dependent upon cell type, intracellular volumes range from 10 to 100 nL. The typical working concentration for an internal standard radical dosimeter is on the order of 1-10 mM. As such, the effective amount of intracellular dosimeter ranges from 10 picomole to 1 nanomole, substantially challenging photometric detection. Under such constraints, photometric absorbance detection will very likely fail to provide sufficient analytical sensitivity to accurately and precisely determine the change of photometric absorbance of an intracellular radical dosimeter upon the introduction of OH radicals. The latter is attributed to the fact that photometric absorbance detection functions by detecting changes in transmitted light of sample when probed by incident light. For solute concentrations below 1 µM, the resultant photometric change in transmitted light becomes measurably indistinct and effectively insignificant when compared to the original intensity of incident light.

Unlike photometric absorbance detection, photometric fluorescence detection functions by detecting small changes of light on a dark background, as detected light is only generated when a fluorescent moiety is illuminated using the appropriate wavelength of excitation light that is prohibited from striking the fluorescence detector. As such, fluorescence detection is on the order of 1,000-10,000 times more sensitive than absorbance detection, and has been successfully applied to imaging and photometric measurements of single cells. For the purpose of radical dosimetry using an internal standard, an ideal fluorescence dosimeter would have: a simple relationship between effective radical concentration and fluorescence response; be unreactive to cellular constituents and biomolecular complement; and not fluoresce unless attacked by oxidative chemistry. There is a preponderance of literature that describes fluorescence moieties that could be used for in vivo dosimetry; however, the vast majority of these compounds are inherently fluorescent. Under such conditions, the use of inherently fluorescent radical dosimeters to detect effective OH radical concentration would be dependent upon detecting the loss of fluorescence upon OH radical attack. As such, these fluorescent probes would provide limited sensitivity akin to that of photometric absorbance, as once again detection would be limited by searching for small changes in light intensity upon a large background.

In various embodiments of the invention, using an intrinsic or extrinsic, intracellular radical dosimeter internal standard, the effective concentration of generated OH radicals can be assessed by comparing the difference in fluorescence signal for irradiated and non-irradiated cells. During protocol development, the measured change in dosimeter fluorescence is compared with in vivo HRPF empirical results to determine the ideal effective OH radical concentration for subsequent experiments. Once a metric for dosimeter fluorescence signal change has been established, the variability in measured dosimeter fluorescence change for all subsequent experiments performed using similar cells and microfluidic conditions can be leveraged as a way to monitor changes in background scavenging. Once background scavenging has been assessed, corrections can be applied to compensate for trial to trial variability as illustrated in FIG. 3. In some methods, photo-irradiance can be altered proportionally with changes in back-ground scavenging. Irradiance can be increased to compensate for increased levels of scavenging or decreased to address decreased levels of scavenging. In some methods, the concentration of $H_2O_2$ can be proportionally adjusted to address variation in intracellular scavenging. In another methods, the measured abundance of the oxidized species, as detected by mass spectrometry or some other detection scheme such as but not limited to isoelectric focusing electrophoresis, in two or more different trials could be normalized between runs by multiplying said response by a normalization factor derived from the ratio of fluorescence signal change for the different trials.

Figure 4:
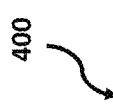
FIG. 4 includes a table 400 of exemplary in vitro fluorescent dosimeter internal standards that can be employed in the present invention along. Each example is listed along with their respective maximum excitation and emission wavelengths, as well as the general intra-cellular compartments within which the fluorescent internal standard dosimeters accumulate. These, of similar compounds can be used individually or in combination.

Exemplary extrinsic fluorescent radical dosimeter internal standards are illustrated table 400 of FIG. 4. The internal standards listed in FIG. 4 are intended to be illustrative and not restrictive in scope, as other internal standards will become obvious in light of the teachings presented here to those of ordinary skill in the art. The dosimeter internal standards listed in FIG. 4 exhibit low inherent fluorescence, and are transformed into fluorescent species upon oxidative attack, and that transformation process is dependent upon the kinetics of oxidative attack, which in turn is dependent upon the yield or concentration of oxidative species. Moreover, all of these internal standards when added to nutrient buffer for cell suspensions or incubated cell lines are readily taken up by said cells. Prior to in vivo HRPF, cells are isolated from their original nutritive buffer by the process of dialyses, buffer exchange, or centrifugation, and then re-suspended in a buffer devoid of dosimeter. During the in vivo HRPF process, cells are mixed with $H_2O_2$ just prior to photolysis. $H_2O_2$ is rapidly and readily taken up by the cells, and when UV photo-irradiated as taught herein, photo-lysed into OH radicals, which rapidly attack intracellular components, including the fluorescent radical dosimeter. Upon oxidation, the radical dosimeters listed in FIG. 4 become brilliantly fluorescent when irradiated with the appropriate excitation wavelength as shown, and the net change in measured fluorescence is dependent upon the effective yield of OH radicals. The fluorescence emission wavelength for each species is also listed.

For some in vivo HRPF studies, it is desirable to analyze the biological complement and bio-physiology of cell organelles, such as the nucleus, when studying DNA replication or DNA-mRNA transcription, or mitochondria, when studying cellular energetics and respiration. Under such circumstances, the use of an in vivo dosimeter internal standard that preferentially compartmentalizes into said organelles is useful and enabling. One such in vivo dosimeter is CellROX® Green, as available from ThermoFisher (USA). CeliROX Green preferentially localizes in the nucleus and mitochondria of eukaryotic cells.

Figure 5:
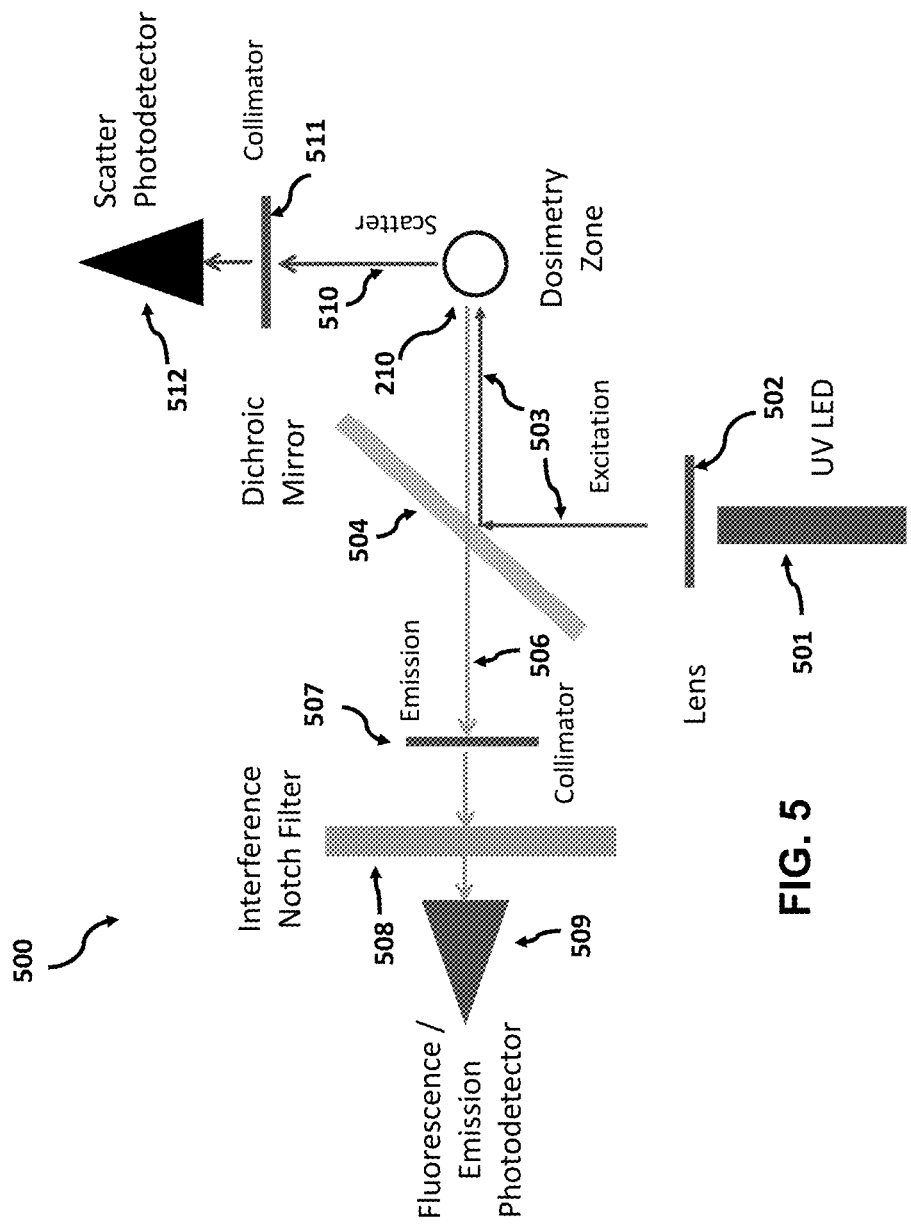
FIG. 5 depicts components of the invention's fluorescence and light scatter photo-detection system, e.g. further details of flash photolysis system, according to various embodiments of the invention. This flash photolysis system can include photolysis zone 102, flash photolysis light 103 and/or radical dosimeter 104 as illustrated in FIG. 1. Shown are: an ultraviolet, narrow bandwidth light source 501 such as an UV light emitting diode or UV diode laser; focusing lens 502; excitation light 503; dichroic mirror 504; dosimetry zone 210; emission light 506 from fluorescence generated within the dosimetry zone 210; collimating lens 507; an interference notch filter 508 that selectively transmits the emission light; a fluorescence/emission light photodetector 509; scattered excitation light 510 from the dosimetry zone 210; collimating lens 511; and scattered light photodetector 512.

As illustrated in FIG. 5, some embodiments include an integrated photometric fluorescence and light scatter detector 500 for in vivo HRPF radical dosimetry. FIG. 5 depicts the salient optical componentry for an integrated photometric fluorescence and light scatter detector 500 for use in in vivo HRPF radical dosimetry. This integrated device provides at least, but not limited to, two basic functions: 1) it provides a system by which fluorescence signal may be generated and detected for an intracellular, internal standard, fluorescence radical dosimeter; and 2) it provides a system by which to detect the entrance of an in vivo entity into the dosimeter zone 210, count the number of in vivo entities that enter the dosimeter zone 210 within a designated time period, determine the size of said in vivo entity or entities, and determine the residence time of a single in vivo entity within the dosimetry zone 210.

Fluorescence detector theory of operation is as follows. Excitation light 503 is provided by a high flux, narrow band-width solid state UV source 501 such as a UV light emitting diode (LED), as available from Q-Photonics (Ann Arbor, MI) or a compact, solid state laser, as available from Thorlabs (Newton, NJ). Typical output power can range from but limited to 0.1-10 mW, and typical bandwidth can range from but not limited to 1 to 15 nm. The wavelength of UV source 501 is selected to be an appropriate choice for the excitation wavelength of the employed in vivo internal standard radical dosimeter. A focusing lens assembly 502 is used to focus excitation light to a narrow beam waste on the order of 1-20 μmeters within the center of the dosimetry zone 210, creating the probed dosimetry zone. Excitation light is directed to strike the dosimetry zone 210 that may contain an in vivo entity or entities, by dichroic mirror 504. Dichroic mirror 504 preferentially reflects light of the excitation wavelength while simultaneously being transparent for light of longer wavelength, such as that of the fluorescence emission light 506. Fluorescence emission light 506 is collimated using collimator 507. After collimation, emission light can be optionally filtered by notch filter 508, to selectively transmit light of the appropriate emission wavelength. Notch filter 508 may be required as collected emission light may be comprised of both fluorescence light as well as a small amount of original excitation light that transmits through dichroic mirror 504, which was created by the back-scatter of excitation light incident to cell optical surfaces and probed contents. Emission light is directed to ultimately strike fluorescence/emission photodetector 509, which serves to measure the intensity of the fluorescence/emission light. Photodetector 509 may comprise a UV responsive silicon photodiode such as the S1336-8BQ silicon photodiode available from Hamamatsu (Hamamatsu City, Japan). Alternatively, photodetector 509 may comprise a compact photo-multiplier tube (PMT) such as Micro PMT assembly H12400 available from Hamamatsu. Photodetector 509 output current is processed by a current to voltage (I to V) convertor to provide a voltage that is proportional to incident emission light intensity 506. Photodetector 509 output voltage is transmitted to control electronics 105, where an analog to digital converter (ADC) creates a digital signal that is ultimately transmitted to the instrument controller 106 where fluorescence calculations are performed.

Light scatter detector theory of operation is as follows. Excitation light 503 from UV source 501 is focused by lens 502 and reflected by dichroic mirror 504 to enter dosimetry zone 210. Upon incidence with an in vivo entity located within the probed region of the dosimetry zone 210, incident excitation light 503 is elastically scattered. Due to the size difference between the incident excitation wavelength (nm) and in vivo entity size (μm), the scattered light 510 is preferentially detected orthogonally with respect to the incident excitation light. Scattered light 510 is collimated by collimator 511 and ultimately strikes scatter photodetector 512. For a given excitation light intensity, the measured intensity of scattered light will be proportional to the size and number of in vivo entities located within the dosimetry zone 210 probed volume. As scattered light detection is being performed in an orthogonal direction with respect to incident excitation light, measured back-ground scatter, in the absence of in vivo entities, attributed to elastic and inelastic scatter of probed volume contents, as well as elastic scatter from radical dosimeter 104 optical surfaces are extraordinarily low, creating a very low background signal.

Scatter Photodetector 512 may comprise a UV responsive silicon photodiode such as the 51336-8BQ silicon photodiode available from Hamamatsu (Hamamatsu City, Japan). Alternatively, photodetector may comprise a compact photo-multiplier tube (PMT) such as Micro PMT assembly H12400 available from Hamamatsu. Scatter photodetector 512 output current is processed by a current to voltage (I to V) convertor to provide a voltage that is proportional to incident scatter light 506. Photodetector 509) output voltage is transmitted to control electronics 105, where an analog to digital converter (ADC) creates a digital signal that is ultimately transmitted to the instrument controller 106 where light scatter calculations are performed.

Various embodiments of the invention include methods of determining and controlling cell-to-cell isolation volume to enable reproducible in vivo radical dosimetry. For in vivo HRPF radical dosimetry to be effectively implemented, photometric measurements of an internal standard radical dosimeter should be performed when the in vivo entity or entities are present within the dosimetry zone, to enable meaningful comparative measurements that represent differences in cell-to-cell, intracellular radical dosimeter response.

Figure 6:
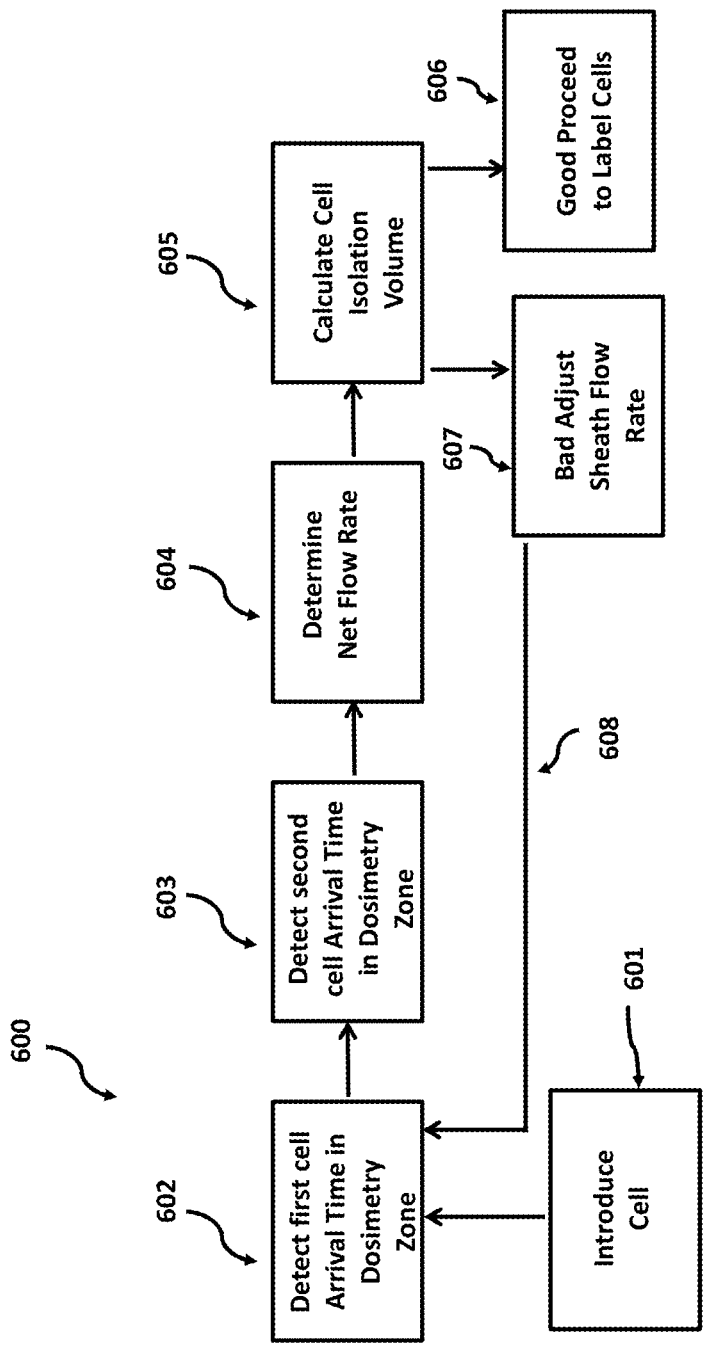
FIG. 6 illustrates methods 600 for establishing a consistent cell isolation volume, according to various embodiments of the invention. Shown are: an introduce cell step 601 in which first one or more cells to be labeled are introduced to a sheath flow configured to isolate individual cells or groups of cells; a detect first cell step 602 in which the arrival of a first cell (or set of cells) introduced in step 601 in the photolysis zone 102 is detected; a detect second cell step 603 in which arrival of a second cell within the photolysis zone 102; a determine net flow step 604 in which a net flow rate (dependent upon sheath flow, hydrogen peroxide, and cell buffer syringe pumps pumping rates) is determined; a determine cell isolation volume step 605, in which a the cell isolation volume is determined as the product of the difference in cell arrival time and the net flow rate; a decision step 606 in which whether or not a desired cell isolation volume has been achieved (the cell isolation volume being a measure of how isolated each cell or group of cells are within the photolysis zone 102; an adjust step 607, performed if the desired cell isolation volume is not achieved, in which flow rates (e.g., of syringe pump 202, 205 and/or 207) are adjusted to better reach the isolation volume and prior steps are repeated 608, and a good step 606 in which the desired isolation volume has been achieved and the process of labeling and analyzing cells can proceed.

FIG. 6 depicts methods 600 of determining and controlling cell-to-cell isolation volume using the described invention herein that further enables the detection of in vivo entities within the dosimetry zone. In an introduce cell step 610, a single file array of cells is formed as described elsewhere herein, and introduced into mixer 203 from which it flows into dosimetry zone 210. In a detect first cell step 602 a signal from Scatter photodetector 512 is monitored to detect the arrival time of said first cell into the dosimetry zone 210. Upon the entrance of a cell or other in vivo biological entity within the dosimetry zone, the intensity of scattered excitation light 510 increases in accordance with the in vivo entity size and number of in vivo entities within the probed region. In a detect second cell step 603 the process described above is used to detect the arrival time of a second cell into the dosimetry zone 210. The net flow rate for the system is calculated 604 by summing the pumping speeds of syringe pump 202, syringe pump 205, and syringe pump 207. The flow rate can be reduced to the point where the time between detection of the first cell and the cell is long enough to reduce the probability that two cells will be in the dosimetry zone 210 at the same time. This achieves single cell isolation in which the conditions allow the irradiation and oxidation of one cell at a time.

In a calculate cell isolation volume step 605, the cell-to-cell isolation volume is determined by multiplying the arrival time difference between the first and second cells by the net flow rate 604. If the empirically determined cell isolation volume deviates by less than +/−5% (or some other predetermined limits) from the desired isolation volume (which is directly related to a separation distance and separation time), then the system proceeds to label additional cells without further adjustment in a proceed step 606. Proceed step 606 optionally includes the methods illustrated in FIG. 3. Optionally, should the empirically determined cell isolation volume deviate by greater than +/−5%, sheath flow syringe pump 207 pumping speed is altered, in an adjust sheath flow rate step 607, to achieve the desired cell isolation target volume 607 and the determination process repeated 608 until target cell isolation volume is achieved.

Various embodiments include systems and method for detecting the presence of in vivo entities within dosimetry zone 210. The detected time of entry and exit of an in vivo entity within the dosimetry zone may be used to determine the data acquisition period for photometrically determining intracellular dosimeter internal standard radical response. Upon entrance into the dosimetry zone 210, the in vivo entity causes a rapid rise in the intensity of scattered light as detected by scatter photodetector 512. Concordantly, upon in vivo entity exit, the intensity of scattered light as detected by scatter photodetector 512 precipitously drops. The time difference between the rise and drop of scattered light intensity represents the dosimetry zone dwell period of the in vivo entity, e.g. cell. During the dwell period, light intensity values as detected by emission photo-detector 509 are summed and/or integrated to determine the net dosimetry signal for the in vivo entity of interest. By employing this approach, photometric dosimetry may be performed by detecting signals that arise from intracellular and/or extracellular photometric signals, while rejecting any inherent background signal that arises from the extracellular fluid for regions devoid of in vivo entities. As such, the majority of the measured photometric signal will be comprised of that which arises from intracellular components, as the background single for extracellular fluid is, by experimental design, substantially lower than that of intracellular fluid, and measurements are exclusively taken in the presence of an in vivo entity or entities.

Some embodiments include systems and methods for determining the viability of in vivo entities. For a given in vivo entity, scattered light intensity will be proportional to the size and number of in vivo entities present within dosimetry zone 210 during photometric assessment. Using the methodology disclosed herein, means to effectively ensure a constant arrival rate of in vivo entities within the dosimetry zone is described. Under such circumstances, the number of in vivo entities for each data acquisition period can be constantly controlled, rendering the variation in measured scattered light to be vastly dependent upon changes in in vivo entity size. Changes of in vivo entity size can be attributed to inherent morphological variation or can be indicative of artifactual alteration in cellular/species morphology, which may be indicative of cellular disruption, cell death, or cellular apoptosis. As the inherent goal of in vivo HRPF is to assess biomolecular complement HOS under viable conditions, it is desirable to detect and signal the presence of inviable processes and/or conditions. Embodiments of the invention described herein provide systems and methods to detect the potential harm to in vivo moieties that may arise from the HRPF protocol, and as such provides a means by which in vivo HOS analysis can be performed for viable and not disrupted in vivo entities. For example, a disrupted cell or the presence of more than one cell within the dosimetry zone 210 at the same time can be detected based on the measured light scattering. These detected entities under these circumstances may be separated from entities that were not irradiated under these conditions and discarded.

Various embodiments of the invention include systems and methods for triggering the flash photolysis light 103 in sync with arrival of an in vivo entity into the photolysis zone 102. In vivo HRPF ideally includes determining and quantitating the presence of an in vivo entity within the photolysis zone in order to reliably irradiate said entity or entities in a reproducible manner and to photo-catalytically create a reproducible, intracellular OH radical load.

Figure 7:
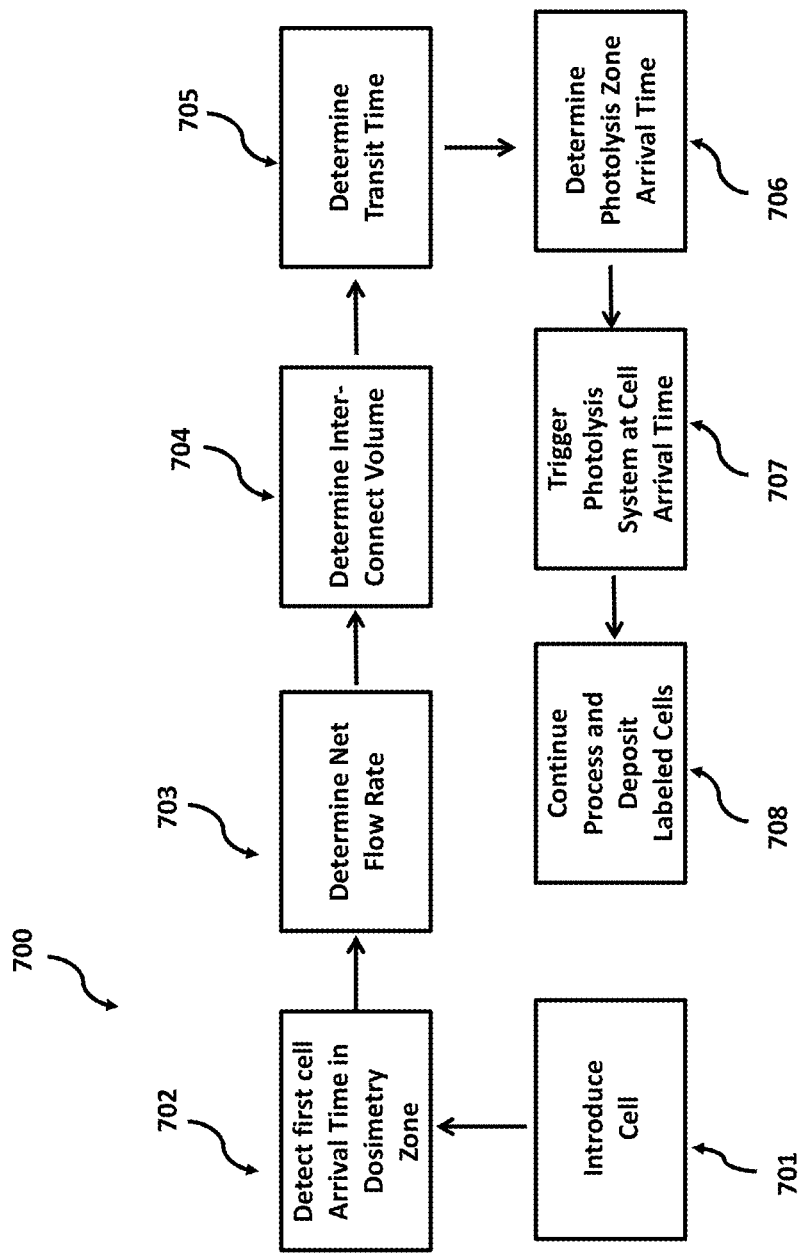
FIG. 7 illustrates methods of coordinating the flash photolysis activity of the photolysis system with the arrival of a cell within the photolysis zone, according to various embodiments. Shown are: an introduction step 701 in which a single isolated cell or group of isolated cells to be labeled are introduced using the focusing sheath flow a detection step 702 in which the arrival of a first cell is detected within the photolysis zone 102, a determine net flow rate step 703, in which the net flow rate is determined based upon sheath flow, hydrogen peroxide, and cell buffer syringe pumps pumping rates; a determine the inter-connect volume step 704 in which a volume between photolysis zone 102 and dosimetry zone 210 (of radical dosimeter 104) is determined; a determine transit time step 705, in which the cell transit time from photolysis zone 102 to dosimetry zone 210 is determined; a determine arrival time step 706, in which the arrival time for the first cell at the photolysis zone 102 is determined; a trigger step 707, in which flash photolysis light 103 is triggered to provide light to the photolysis zone 102 at the arrival time determined in step 706; and a continue step 708, in which the process is repeated for additional cells.

FIG. 7 depicts methods 700 of determining the arrival of an in vivo entity into the photolysis zone 102, while providing systems and methods by which the flash photolysis light 103 is precisely triggered to flash upon the arrival of the in vivo entity into said photolysis zone. In an introduce cell step 701 a single file array of cells is formed as described elsewhere herein, and a first cell is introduced into photolysis zone 102. In a detect step 702 the output signal of scatter photodetector 512 is monitored to detect the arrival time of said first cell into the dosimetry zone 102. Upon the entrance of a cell or other in vivo entity within the dosimetry zone 102, the intensity of scattered light increases in accordance with the in vivo entity size and number of in vivo entities within the probed region. This increase is detected by scatter photodetector 512. In a determine net flow rate step 703, the net flow rate for the system is calculated by summing the pumping speeds of syringe pump 202, syringe pump 205, and syringe pump 207. In a determine interconnect volume step 704, as a direct manifestation of the microfluidic system design, the interconnect volume that extends from the photolysis zone and the dosimetry zone is determined and remains constant during the in vivo HRPF process. In a determine transit time step 705, the transit time required for an in vivo entity to travel from the photolysis zone 102 to the dosimetry zone 210 is calculated by dividing the interconnect volume by the net flow rate. In a determine photolysis zone arrival time step 706, the photolysis zone arrival time is calculated by determining the difference of the dosimetry zone arrival time and the photolysis zone to dosimetry zone transit time. In a trigger step 707, for subsequent cells or in vivo entities, the photolysis system is triggered to flash at the determined photolysis zone arrival time or a consistent interval thereafter. In a continue process step 708, the process proceeds and additional labeled cells are deposited within labeled cell reservoir 211 until a target number of cells has been processed.

While the teachings herein describe particular utility of detection signals that arise from light scatter photodetector 512 and fluorescence/emission photodetector 509, it will be obvious to those of ordinary skill in the art that the afore said detectors could be used for the purpose of detecting in vivo entity arrival into the dosimetry zone 210 or for the purpose of predicting the arrival of an in vivo entity into the photolysis zone 102 by a plurality of undescribed combinations or means. For example, signals generated at fluorescence/emission photodetector 509 could be summed in temporal coherence with those from light scatter photodetector 512 to improve the overall sensitivity to detect the presence of an in vivo entity within the dosimetry zone. As such, the methodologies described herein are intended to be exemplary and not restrictive in scope.

Various embodiments of the invention include systems and methods of calibrating a closed-loop control radical dosimetry system. In these embodiments, the closed-loop control radical dosimetry system comprises calibration logic that is used to predict the required change in optical fluence or hydrogen peroxide concentration in response to measured radical dosimeter photometric fluorescence change. The calibration function is empirically determined through a plurality of measurements for which a known or control mixture of supporting buffer, in vivo entity, and radical dosimeter are treated with a single flash of light for each distinct control aliquot at a various fluence or $H_2O_2$ concentration levels. In an exemplary embodiment, a software routine running in either the low level instrument control or high level user interface programs (e.g., control electronics 105 and/or instrument controller 106), generates a look-up table or curve fit that describes the measured change in dosimeter photometric fluorescence at each fluence or $H_2O_2$ concentration, allowing for the creation of a mathematical expression, or calibration function, that describes the relationship between applied fluence and/or $H_2O_2$ concentration and measured dosimeter fluorescence change for a single flash exposure. In another embodiment, the look-up table and subsequent calibration function is manually generated by the user employing fluorescence change values for each flash voltage value and/or $H_2O_2$ concentration.

During in vivo HRPF processing, background hydroxyl radical scavenging is assessed via dosimetry. The measured change in dosimeter photometric fluorescence is compared to a user specified targeted change. When the measured dosimeter value deviates by ≥+/−10% from the target value, the applied fluence or $H_2O_2$ concentration is altered to achieve the targeted change of measured dosimeter absorbance. The above calibration function is used to predict the required change in fluence or $H_2O_2$ concentration.

Various embodiments of the invention include post-analytical normalization of labeled product abundance. In these embodiments, spectral irradiance and/or $H_2O_2$ concentration is altered to adjust for unwanted changes in background scavenging of OH radicals and, as such, represents a pre-analytical or pre-data processing scheme of correction. It is also possible to apply scavenging correction to acquired HRPF data in a post-analytical or data processing manner During post-analytical correction, the measured abundance of the oxidized species for an experimental trial, as detected by mass spectrometry or some other detection scheme such as but not limited to isoelectric focusing electrophoresis, is normalized by multiplying said response by a normalization factor derived from the ratio of dosimeter fluorescence change determined between the experimental trial and reference trial. Specifically, the normalization factor is the ratio of the measured dosimeter fluorescence change of the experimental trial divided by the measured dosimeter fluorescence change of the reference trial. Alternatively, the normalization factor could comprise the ratio of the measured dosimeter fluorescence change of the reference trial divided by the experimental trial. In this manner, for example, the ion current for a given protein mass spectrometry (MS) measurement or peptide single MS or tandem MS measurement could be adjusted by multiplying said ion current value by the determined normalization factor. The application of pre-analytical and post-analytical normalization schemes are not mutually exclusive, and could be employed alternatively or in tandem to achieve higher levels of compensation than achievable otherwise. In one embodiment, post-analytical normalization is applied to data acquired from in vivo HRPF experiments performed under the control of pre-analytical scavenging correction.

In vivo Radical Dosimetry System for Hydroxyl Radical Protein Foot-Printing have been disclosed. It should be apparent, however, to those skilled in the art that many more modifications besides those already described are possible without departing from the inventive concepts herein. The inventive subject matter, therefore, is not to be restricted except in the spirit of disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be presented or utilized, or combined with other elements, components, or steps that are not expressly referenced.

While biological cells are used herein to illustrate various embodiments of the invention, in alternative embodiments, the "cells" may be replaced, in any examples or claims, by other entities such as non-biological entities, biological entities, viruses, multi-cellular organisms (e.g., fungi, spores, nanobes, molds, algae, nematodes, amoeba, protozoa, *Trichoplax adhaerens* or yeasts) or non-biological materials.

The general structure and techniques, and more specific embodiments which can be used to effect different ways of carrying out the more general goals are described herein. Although only a few embodiments have been disclosed in detail above, other embodiments are possible and the inventor intends these to be encompassed within this specification. The specification describes specific examples to accomplish a more general goal that may be accomplished in another way. This disclosure is intended to be exemplary, and the claims are intended to cover any modification or alternative that might be predictable to a person having ordinary skill in the art.

The logic discussed herein can include electronic circuits, hardware, firmware, and/or software store on a non-transient computer readable medium.

Also, the inventors intend that only those claims which use the words "means for" are intended to be interpreted under 35 USC 112, six paragraph. Moreover, no limitations from the specification are intended to be read into any claims, unless those limitations are expressly included in the claims. The computers described herein may be of any kind of computer, either general purpose, or some specific purpose computer such as a workstation or laboratory or manufacturing equipment. The computer may be an Intel (e.g., Pentium or Core 2 duo, i3 etc.) or AMD based computer, running Windows 10, 8, 7, or Linux, or may be a Macintosh computer. The computer may also be a hand-held computer such as a PDA, cellphone, tablet, or laptop, running any available operating system including Android, Windows Mobile, iOS, etc.

Copyright Notice: Pursuant to 37 C.F.R. 1.71(e), applicant notes that a portion of this disclosure contains material that is subject to and for which is claimed copyright protection (such as, but not limited to, source code listings, screen shots, user interfaces, or user instructions, or any other aspects of this submission for which copyright protection is or may be available in any jurisdiction). The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

Want is claimed:

1. An analysis system comprising:
   a sample introduction system configured to provide intact biological entities to a photolysis zone, the biological entities being isolated from each other in a focused sheath flow;
   a photolysis light source configured to generate light to generate hydroxide radicals from a source of hydroxide radicals;
   a photolysis zone configured to receive the sheath flow and the light so as to oxidize an internal standard and so as to oxidize biological compounds of the biological entities in vivo;
   a dosimetry zone configured to receive the biological entities from the photolysis zone, and to detect oxidation of the internal standard using a fluorescence detector;
   control logic configured to determine that a target concentration of hydroxide radicals was generated for each of the biological entities and to adjust operation of the photolysis zone to meet the target concentration of hydroxide radicals; and
   a reservoir configured to receive the biological entities including the oxidized biological compounds.

2. The system of claim 1, further comprising an analyzer configure to identify peptides or amino acids oxidized in the photolysis zone, the analyzer optionally being configured to separate peptides based on mass, charge or size.

3. The system of claim 1, wherein the sample introduction system is configured to isolate the biological entities from each other using a sheath flow.

4. The system of claim 1, wherein the sample introduction system is configured to add the source of hydroxide radicals to the biological entities.

5. The system of claim 1, wherein the internal standard is intrinsic to a buffer with which the biological entities were mixed, and the internal standard is configured to be absorbed into an interior of the biological entities, and/or the internal standard is configured to be adsorbed onto a surface of the biological entities.

6. The system of claim 1, wherein the source of hydroxide radicals is $H_2O_2$.

7. The system of claim 1, wherein the scattered light detector is configured to determine that the biological entities are intact.

8. The system of claim 1, wherein the dosimetry zone if further configured to detect presence of the biological entities using a scattered light detector.

9. The system of claim 1, wherein the control logic is configured to determine a time the light is received by the biological entities in the photolysis zone based on detection of fluorescence or scattered light in the dosimetry zone.

10. The system of claim 1, wherein the control logic is configured to adjust the operation of the photolysis zone by changing a concentration of the source of hydroxide radicals, changing a flow rate, changing an amount of the light received from the photolysis light source, and/or changing a time at which the light is received from the photolysis light source.

11. The system of claim 1, wherein the control logic is configured to determine a time period between which isolated members of the biological entities enter the photolysis zone.

12. The system of claim 1, wherein the control logic is configured to control flow of the biological entities to the reservoir such that ruptured biological entities are diverted from the reservoir.

13. The system of claim 1, wherein the control logic is configured to normalize a quantitation of the identified peptides based on a fluorescence signal from the internal standard within the dosimetry zone.

14. The system of claim 1, wherein the control logic is configured to provide feedback to the sample introduction system or the photolysis light source based on analysis of a first of the biological entities to improve analysis of a second of the biological entities.

15. A method of oxidizing biomolecules within an intact cell, the method comprising:
   introducing a sample mixture containing at least one cell into a photolysis zone, a source of hydroxide radicals and a dosimeter internal standard into a photolysis zone of a flash photolysis system;
   providing light to generate the hydroxide radicals from the source of hydroxide radicals, the hydroxide radicals being configured to oxidize biomolecules within the at least one cell;
   waiting a time for the at least one cell to reach a dosimetry zone of a radical dosimeter configured to detect a photometric property of the dosimeter internal standard resulting from reaction of the dosimeter internal standard and the hydroxide radicals, wherein the at least one cell is detectable within a dosimetry zone of the radical dosimeter by light scattering;
   measuring a photometric property of the dosimeter internal standard using the radical dosimeter, while the at least once cell is within the dosimetry zone;
   determining that a target level of hydroxide radicals was not generated based on the measured photometric property of the dosimeter internal standard; and
   adjusting a concentration of hydroxide radicals within the photolysis zone by adjusting at least one of: 1) an amount of light provided to the photolysis zone, 2) a concentration of the source of hydroxide radicals, 3) a flow rate of the at least once cell within the photolysis zone, or 4) adjusting a time of providing the light to the photolysis zone.

16. The method of claim 15, further comprising:
   introducing at least a second cell into the photolysis zone;
   providing light to generate the hydroxide radicals, at the adjusted concentration, from the source of hydroxide radicals, to oxidize biomolecules within the second cell, the;
   waiting a time for the second cell to reach a dosimetry zone of a radical dosimeter;
   measuring a photometric property of the dosimeter internal standard using the radical dosimeter, while the second cell is within the dosimetry zone;
   determining that a target level of hydroxide radicals was generated based on the measured photometric property of the dosimeter internal standard, while the second cell was within the dosimetry zone; and collecting the second cell for in vivo three-dimensional structural analysis of biomolecules of the second cell based on oxidation of the biomolecules within or on the surface of the second cell.

17. The method of claim 15, further comprising:

placing the at least one cell in a buffer solution including the dosimeter internal standard for a time sufficient for the dosimeter internal standard to migrate into an interior of the at least one cell; and rinsing the at least one cell to remove the dosimeter internal standard from extracellular solution surrounding the at least one cell, prior to introducing the sample mixture containing the at least one cell into the photolysis zone of the flash photolysis system.

18. The method of claim 15, wherein the dosimeter internal standard is intrinsic to the buffer solution.

19. The method of claim 15, wherein the dosimeter internal standard includes at least one of terepthalic acid, dichlorofluoroscein, CellROX Green, CellROX Orange, or CellROX Deep Red.

20. The method of claim 15, wherein the dosimeter internal standard is configured to be absorbed into an interior of the at least one cell.

21. The method of claim 15, wherein the at least once cell is part of a plurality of cells introduced into the photolysis zone and each of the plurality of cells separated from a next of the plurality of cells by a same isolation volume.

22. The method of claim 15, wherein the photometric property is fluorescence or luminescence.

23. The method of claim 15, wherein the dosimetry zone is configured to simultaneously detect both a fluorescence signal and a light scattering signal from the at least one cell.

24. The method of claim 15, wherein the concentration of hydroxide radicals are adjusted by changing the amount of light provided.

25. The method of claim 15, further comprising identifying amino acids within the at least one cell that were oxidized by the hydroxide radicals within the photolysis zone.

26. The method of claim 15, further comprising normalizing an analysis of oxidation of the at least one cell based on the photometric property of the dosimeter internal standard.

27. The method of claim 15, wherein the at least one cell includes a plurality of cells and sample mixture is introduced in a sheath flow configured to place each member of the plurality of cells in single file separated by approximately the same distance from each other.

28. The method of claim 15, wherein a light scattering signal within the dosimetry is used to determine a time for providing the light to generate the hydroxide radicals.

29. The method of claim 15, further comprising determining that the second cell was intact based on a scattering signal detected within the radical dosimeter.

30. The system of claim 15, wherein the analyzer is configured to detect oxidation of an isotopically labeled nucleic acid, amino acid, lipid, carbohydrate or peptide.

* * * * *

UNITED STATES PATENT AND TRADEMARK OFFICE
CERTIFICATE OF CORRECTION

| | | |
|---|---|---|
| PATENT NO. | : 12,016,688 B2 | Page 1 of 1 |
| APPLICATION NO. | : 17/411855 | |
| DATED | : June 25, 2024 | |
| INVENTOR(S) | : Scot Randy Weinberger | |

It is certified that error appears in the above-identified patent and that said Letters Patent is hereby corrected as shown below:

In the Specification

Column 1, Lines 37-41, please delete:
"The invention described in this patent application was made with support from the U.S. government through National Institute of General Medical Sciences grant awards R43 GM 137728-01 and R44 GM 137728-02. As such, the U.S. government has certain rights to the invention."

And insert therefore:
--This invention was made with government support under grant number R43 GM137728 awarded by the National Institutes of Health. The government has certain rights in the invention.--

Signed and Sealed this
Fourth Day of March, 2025

Coke Morgan Stewart
*Acting Director of the United States Patent and Trademark Office*